US006028088A

United States Patent [19]
Pershadsingh et al.

[11] Patent Number: 6,028,088
[45] Date of Patent: Feb. 22, 2000

[54] FLAVONOID DERIVATIVES

[75] Inventors: Harrihar A. Pershadsingh, Bakersfield, Calif.; Mitchell A. Avery, Oxford, Miss.

[73] Assignee: The University of Mississippi, University, Miss.; by said Mitchell A. Avery

[21] Appl. No.: 09/183,798

[22] Filed: Oct. 30, 1998

[51] Int. Cl.[7] .................. A61K 31/42; A61K 31/425; C07D 413/12; C07D 417/12
[52] U.S. Cl. .................. 514/369; 514/359; 514/376; 548/100; 548/183; 548/226
[58] Field of Search .................. 548/183; 514/369

[56] References Cited

U.S. PATENT DOCUMENTS

| | | | |
|---|---|---|---|
| 3,450,717 | 6/1969 | Krämer et al. | 260/340.5 |
| 3,878,191 | 4/1975 | Fukumoto et al. | 260/210 F |
| 4,079,139 | 3/1978 | Gay | 424/248.58 |
| 4,572,912 | 2/1986 | Yoshioka et al. | 514/369 |
| 4,697,020 | 9/1987 | Storni et al. | 548/184 |
| 4,841,077 | 6/1989 | Ito et al. | 549/402 |
| 4,886,806 | 12/1989 | Walenta et al. | 514/253 |
| 4,889,941 | 12/1989 | Wu et al. | 549/403 |
| 4,970,301 | 11/1990 | Rolland et al. | 536/8 |
| 5,012,852 | 5/1991 | Walenta et al. | 549/362 |
| 5,120,754 | 6/1992 | Clark et al. | 514/369 |
| 5,126,129 | 6/1992 | Wiltrout et al. | 424/85.2 |
| 5,130,379 | 7/1992 | Clark et al. | 514/333 |
| 5,143,930 | 9/1992 | Yoshioka et al. | 514/369 |
| 5,280,024 | 1/1994 | Bolland et al. | 514/233.5 |
| 5,338,855 | 8/1994 | Yoshioka et al. | 514/369 |
| 5,431,912 | 7/1995 | N'Guyen | 424/401 |
| 5,441,971 | 8/1995 | Sohda et al. | 514/342 |
| 5,554,519 | 9/1996 | Weber et al. | 435/125 |
| 5,594,015 | 1/1997 | Kurtz et al. | 514/369 |
| 5,599,826 | 2/1997 | Mertens et al. | 514/364 |

FOREIGN PATENT DOCUMENTS 62-234085   10/1987   Japan .

OTHER PUBLICATIONS

Comrie, et al., "Some 2–iminoselenazolidin–4–ones and related compounds," *J. Pharm. Pharmacol.* 16:268–272 (1964).

Hulin, et al., "Novel thiazolidine–2,4–diones as potent euglycemic agents," *J. Med. Chem.* 35:1853–1864 (1992).

Lehmann, et al., "An antidiabetic thiazolidinedione is a high affinity ligand for peroxisome proliferator–activated receptor γ (PPARγ)" *J. Biol. Chem.* 270(22):12953–12956 (1995).

Wilson, et al., "The Structure—Activity relationship between peroxisome profliferator–activated receptor γ agonism and the antihyperglycemic activity of thiazolidinediones," *J. Med. Chem.* 39:665–668 (1996).

Muller, et al., "Ligands for peroxisome proliferator–activated receptorgamma and retinoic acid receptor inhibit growth and induce apoptosis of human breast cancer cells in vitro and in BNX mice" (Abstract only) *Proc. Natl. Acad. Sci. U.S.A.* 95(15):8806–11 (Jul. 21, 1998).

Johnson, et al., "Structural requirements and cell–type specificity for ligand activation of peroxisome proliferator–activated receptors," (Abstract only) *J. Steroid Biochem. Mol. Biol.* 63(1–3):1–8 (Sep.–Oct. 1997).

*Primary Examiner*—Laura L. Stockton
*Attorney, Agent, or Firm*—Townsend and Townsend and Crew LLP

[57] ABSTRACT

The present invention provides thiazolidinediones which are useful as antiproliferative, antiinflammatory and antiinfective agents. These compounds are useful for the treatment of certain endocrine diseases including diabetes, certain malignant and non-malignant proliferative diseases including prostate cancer, breast cancer, psoriasis, and acne, certain cardiovascular disorders including hypertension and occlusive vascular diseases.

31 Claims, 16 Drawing Sheets

1, n = 1; 2, n = 2; 3, n = 3; 4, n = 4; 5, n = 5

6      Rutinose

Key: a) CH₃OCH₂Cl (MEM-Cl), NaH; b) 4-chloro-nitrobenzene; c) AcOH, H₂SO₄; d) Ac₂O, pyridine; e) H₂, Pd/C, EtOH; f) HONO; then CH₂=CHCOOEt, CuO; g) thiourea, sulfolane; h) then HCl, HOH,.

B

A

Key: a) ClCH$_2$CH$_2$OH, NaOH, Δ; b) H$_3$O$^+$.

B

Key: a) Me$_2$SO$_4$, acetone, Na$_2$CO$_3$, Δ; b) HCl, H$_2$O.

A

B

A

B

40, n = 2; correpsonds to 1
41, n = 3; corresponds to 2

A

52, n = 1; 53, n = 2; 54, n = 3; 55, n = 4; 56, n = 5

B

57, n = 1; 58, n = 2; 59, n = 3;
60, n = 4; 61, n = 5

C

57-61; $R_1$ = Me, Et; X-R = OH        52-56 guanidine; hydrolysis

A

B

A

79, n = 1; 80, n = 2; 81, n = 3; 82, n = 4; 83, n = 5

84

B

Key: a) $BF_3 \cdot OEt_2$, 51% yield; b) Microwave, $(MeO)_2CHNMe_2$, THF, 91% yield.

FLAVONOID DERIVATIVES

BACKGROUND OF THE INVENTION

Peroxisome proliferator-activated receptors (PPARs) are members of the nuclear receptor superfamily of ligand-activated transcription factors. Three subtypes of PPARs have been cloned from the mouse and human: i.e., PPARα, PPARγ and PPARδ. The PPARs are believed to play a role in the regulation of lipid metabolism. They can be activated by fatty acids and have been shown to regulate the expression levels of binding proteins and enzymes involved in fatty acid oxidation.

It has previously been discovered that a certain class of thiazolidinediones are selective PPARγ agonists. (see, Willson et. al., *J. Med. Chem* (1996) 39:665–668). Thiazolidinediones are a class of oral insulin-sensitizing agents that improve glucose utilization without stimulating insulin release. For instance, U.S. Pat. No. 4,287,200 discloses certain thiazolidine derivatives having the ability to lower blood glucose sugar levels. In addition, U.S. Pat. No. 4,572,912 discloses thiazolidinedione derivatives having the ability to lower blood lipid and blood sugar levels. These compounds were shown to have the ability to decrease the levels of blood lipid peroxides, blood triglycerides and blood cholesterol.

Moreover, U.S. Pat. No. 5,338,855 discloses thiazolidine derivatives containing a quinone moiety. These compounds were shown to have the ability to reduce insulin resistance in the peripheral tissues and possess the ability to suppress hepatic gluconeogenisis in the liver.

In addition to being anti-diabetic agents which can lower the concentration of glucose and lipids in the blood, U.S. Pat. No. 5,594,015 discloses thiazolidine derivatives as being effective in the treatment of hyperproliferation of epithelial cell conditions, such as psoriasis.

The anti-diabetic effect of the thiazolidinediones and their PPARγ agonist activity has implicated PPARγ as the molecular target for the anti-diabetic effects of thiazolidinediones. PPARγ is predominately expressed in adipose tissue and has been implicated as a master regulator of adipocyte differentiation in pre-adipose cell lines.

In view of the role PPARγ plays in regulation of lipid metabolism and the antagonistic behavior of thiazolidinediones, there remains a need in the art for new thiazolidinedione derivatives and more effective therapies for diabetes and other ailments. As such, the present invention fulfills these and other needs.

SUMMARY OF THE INVENTION

The present invention provides new thiazolidinedione derivatives. As such, in one aspect, the present invention provides compounds of Formula I:

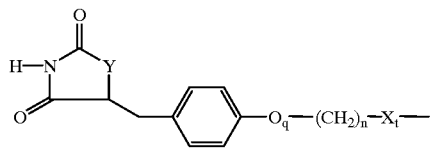

I

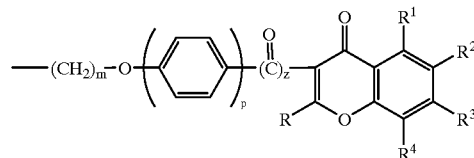

-continued

In Formula I, Y is a heteroatom including, but not limited to, sulfur, selenium or oxygen. X, in Formula I, is a heteroatom including, but not limited to, oxygen, selenium sulfur or $NR^6$, wherein $R^6$ is a functional group including, but not limited to, hydrogen and optionally substituted ($C_1$–$C_{10}$) alkyl. $R^1$, $R^2$, $R^3$ and $R^4$, in Formula I, are functional groups which can be the same or different and include, but are not limited to, hydrogen, hydroxy, halogen, optionally substituted ($C_1$–$C_6$)alkyl, optionally substituted ($C_1$–$C_{20}$)alkoxy, ($C_1$–$C_6$)alkylcarbonyl, ($C_1$–$C_{20}$)alkenyl, $R^{24}R^{23}N(CH_2)_x CH(OH)(CH_2)_y O$—, optionally substituted aroyl, or aryl ($C_1$–$C_{10}$)alkylcarbonyl. R, in Formula I, is a functional group including, but not limited to, hydrogen, phenyl, 3,4-dihydroxyphenyl or $R^{11}$. $R^{11}$, of Formula I, is a functional group including, but not limited to, —A—$NR^{13}R^{14}$, —$CONHR^{15}$, —A—S—$R^{16}$ or —$COOR^{17}$, where A is a lower alkylene group. In Formula I, $R^{13}$ and $R^{14}$ are functional groups which can be the same or different and include, but are not limited to, hydrogen, ($C_1$–$C_6$)alkyl, cycloalkyl or a sulfur- and a nitrogen-containing 5- or 6-membered heterocyclic ring, where the heterocyclic ring may be optionally substituted by one or two hydroxyl groups. In an alternative embodiment, $R^{13}$ and $R^{14}$ together with the nitrogen to which they are bound, form a pyrrolidine, piperidine or morpholine ring. $R^{15}$, in Formula I, is a functional group including, but not limited to, hydrogen, or optionally substituted ($C_1$–$C_6$)alkyl. $R^{16}$, in Formula I, is a functional group including, but not limited to, ($C_1$–$C_6$)alkyl or a sulfur- and nitrogen containing 5- or 6-membered heterocyclic ring, where the heterocyclic ring may be optionally substituted by one or two hydroxyl groups, carboxyl groups, or ($C_1$–$C_6$) alkoxycarbonyl groups. $R^{17}$, in Formula I, is a functional group including, but not limited to, an optionally substituted ($C_1$–$C_6$)alkyl. $R^{23}$, in Formula I, is a functional group including, but not limited to, hydrogen or optionally substituted ($C_1$–$C_6$)alkyl. $R^{24}$, in Formula I, is a functional group including, but not limited to, phenyl, benzyl, and $R^{25}(CH_2)_s CH(T)(CH_2)_k$, or a heterocyclic ring having the formula:

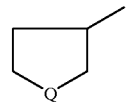

In an alternative embodiment, $R^{24}$, $R^{23}$ and the nitrogen atom to which they are bound form a 5- or 6-membered heterocyclic ring having the formula

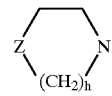

$R^{25}$, in Formula I, is a functional group including, but not limited to, phenoxy or unsubstituted, monosubstituted, or disubstituted Ar, where Ar is an aromatic system including, but not limited to, phenyl, pyridinyl, furanyl, thiophenyl, naphthyl, where each substituent of monosubstituted Ar is the same or different and includes, but is not limited to, hydroxy, $(C_1-C_6)$alkoxy, or $O(CH_2)_rCO_2R^{23}$, each substituent of disubstituted Ar is independently hydroxy or $(C_1-C_6)$ alkoxy. Q, in Formula I, is a functional group including, but not limited to, $SO_2$, S, or O. In Formula I, the index "x" is an integer from 1 to 5; the index "y" is an integer from 1 to 5; the index "h" is an integer from 1 to 2; the index "k" is an integer from 1 to 7; the index "r" is an integer from 1 to 2; and the index "s" is a integer from 0 to 6. T, in Formula I, is a functional group including, but not limited to, hydrogen or OH. Z, in Formula I, is a functional group including, but not limited to, $CH_2$, O, NH, $NCH_3$, and

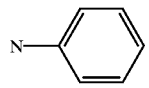

In Formula I, the index "q" is an integer from 0 to 1; the index "n" is an integer from 0 to 5; the index "t" is an integer from 0 to 1; the index "m" is an integer from 0 to 2; the index "p" is an integer from 0 to 1; the index "z" is an integer from 0 to 1; provided that (1) at least one of x and y is one and (2) s plus k total no more than 7.

In another aspect, the present invention relates to a pharmaceutical composition comprising a compound of the Formula I, wherein Y, X, NR6, $R^1$, $R^2$, $R^3$ and $R^4$, R, $R^{11}$, A, $R^{13}$, $R^{14}$, $R^{15}$, $R^{16}$, $R^{17}$, $R^{23}$, $R^{24}$, $R^{25}$, A, Q, x, y, h, s, k, r, s, T, Z, q, n, t, m, p and z have the same meaning as defined above, or a pharmaceutical acceptable salt or solvate thereof, and a pharmaceutical acceptable carrier.

In yet another aspect, the present invention relates to a method of treating a PPARγ mediated disease, comprising administering a therapeutically effective amount of a compound of the of the Formula I to an individual suffering from a PPARγ mediated disease. In other aspects, this invention provides methods for synthesizing the compounds of Formula I.

DETAILED DESCRIPTION OF THE INVENTION

I. Glossary

Figure 1:
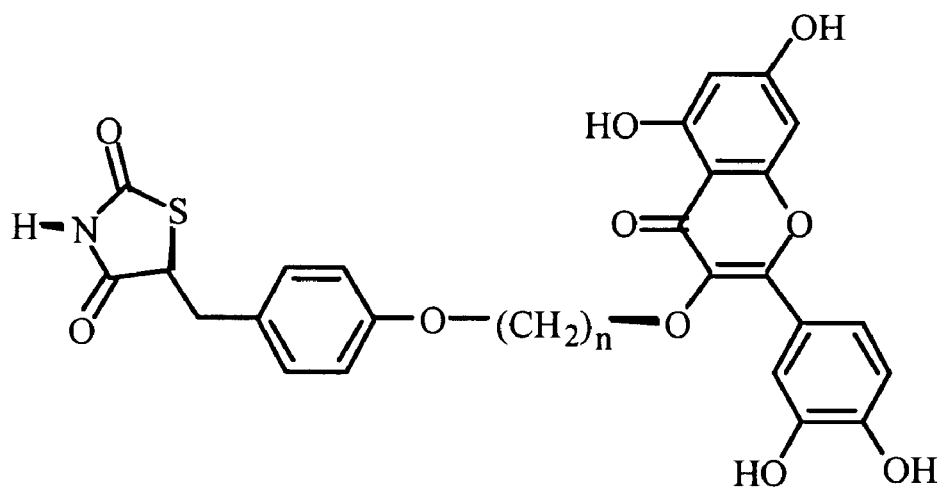
FIG. 1 illustrates compounds of the present invention and potential intermediates in the synthesis of compounds of the present invention.
Figure 1:
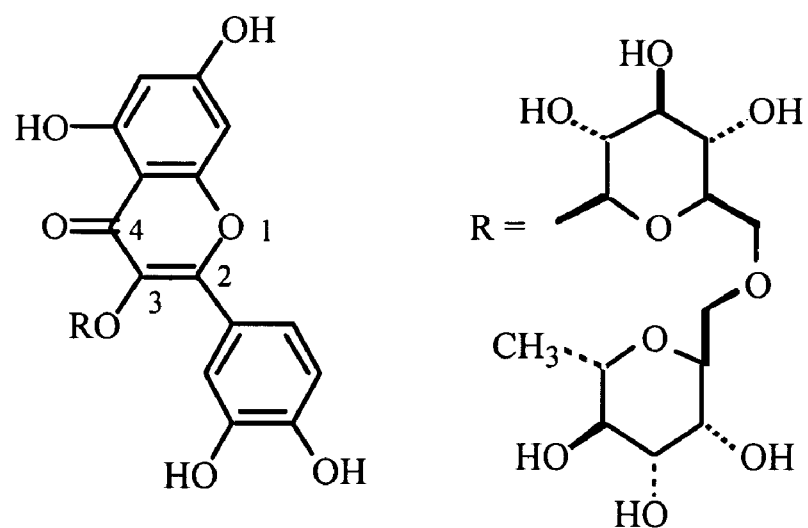

As used herein, the term "alkyl" denotes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "lower" herein means a linear or branched chain of 1 to 6 carbon atoms. Hence, "lower alkyl radicals" represent linear or branched alkyl groups of 1 to 6 carbon atoms, illustrative examples including methyl, ethyl, propyl, isopropyl, butyl, isobutyl, sec-butyl, tert-butyl, pentyl, isopentyl, neopentyl, tertpentyl, 1-methylbutyl, 2-methylbutyl, 1,2-dimethylpropyl; 1-ethylpropyl, hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

The term "alkylene" or "lower alkylene radicals" refers to a divalent alkyl as defined above, such as methylene (—$CH_2$—), propylene (—$CH_2CH_2CH_2$—), chloroethylene (—$CHClCH_2$—), 2-thiobutene —$CH_2CH(SH)CH_2CH_2$, 1-bromo-3-hydroxyl-4-methylpentene (—$CHBrCH_2CH(OH)CH(CH_3)CH_2$—), methylethylene, trimethylene, 1-propylene, 2-propylene, tetramethylene, 1-methyltrimethylene, 2-methyltrimethylene, 3-methyltrimethylene, 1-ethylethylene, 2-ethylethylene, pentamethylene, 1-methyltetramethylene, 2-methyltetramethylene, 3-methyltetramethylene, 4-methyltetramethylene and hexamethylene and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl. The term "lower alkoxy radicals" there may be mentioned linear and branched alkoxy groups of 1 to 6 carbon atoms, such as methoxy, ethoxy, propoxy, isopropoxy, butoxy, isobutoxy, secbutoxy, tert-butoxy, pentyloxy, isopentyloxy, hexyloxy and isohexyloxy groups.

The term "amido" denotes an amide linkage: —C(O)NR— (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "carbonate" indicates —OC(O)O—.

The term "carbamate" denotes —NHC(O)O—, and the term "urea" denotes —NHC(O)NH—.

The term "$EC_{50}$" refers to the concentration of a compound required to activate 50% of the receptors that bind the compound present in a sample or a subject. Thus, in the present invention, the $EC_{50}$ of a PPARγ modifier is the concentration of the modifier that activates 50% of the PPARγ present in the sample or organism. The term "activate" has its ordinary meaning, i.e., cause to function or act.

The term "peroxisome proliferator activating receptor-gamma" or "PPARγ" refers to either the $γ_1$, $γ_2$ or $γ_3$ isotypes or a combination of all isotypes of PPARγ. PPARs are nuclear receptors which naturally bind to fatty acids and which have been implicated in adipocyte differentiation (Perlmann & Evans, Cell 90:391–397 (1997)).

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, transdermal patches, liposomes, teaspoonfuls, tablespoonfuls, dropperfuls, ampoules, vials, aerosols with metered discharges, segregated multiples of any of the foregoing, and other forms as herein described.

II. Thiazolidinedione Compounds and Synthesis

This invention provides flavonoid thiazolidine, oxazolidine and α-substituted carboxylic acid derivatives with antiproliferative, antiinflammatory, antidiabetic, and antiinfective properties, and their use in the treatment of proliferative (malignant and nonmalignant), inflammatory, cardiovascular, endocrine, and viral diseases in human and vertebrate animals. As such, in one aspect, the present invention relates to a compound of Formula I:

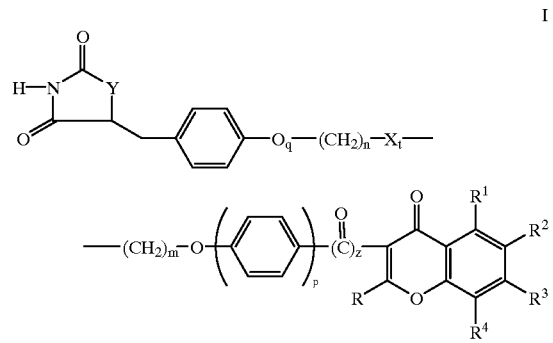

I wherein Y, X, $NR^6$, $R^1$, $R^2$, $R^3$ and $R^4$, R, $R^{11}$, A, $R^{13}$, $R^{14}$, $R^{15}$, $R^{16}$, $R^{17}$, $R^{24}$, $R^{25}$, A, Q, x, y, h, s, k, r, s, T, Z, q, n, t, m, p and z have the same meaning as defined above.

In one preferred embodiment, Y is a heteroatom, such as S and O; X is O, S or $NR^6$, wherein $R^6$ is hydrogen or optionally substituted ($C_1$–$C_6$)alkyl; R is hydrogen or 3,4-dihydroxyphenyl; $R^1$ and $R^3$ are each hydroxy; $R^2$ and $R^4$ are each hydrogen; q is an integer from 0 to 1; n is an integer from 0 to 5; t is an integer from 0 to 1; m is an integer from 0 to 2; p is an integer from 0 to 1; and z is 0.

With reference to FIG. 1, the attachment of an alkyl chain to the flavone moiety of target compounds 1–5, requires no fundamental modification to the aromatic ring system. It is believed that the antioxidant effects of the flavones are dependent upon the free phenolic oxygen atoms, as well as the heterocyclic ring: the 4H-1-chromanone. When the 3-hydroxy group of quercitin (6, R is H) is functionalized, such as in rutin (6, R is rutinose, a deoxy mannopyranoglucoside), the antioxidant effect is retained. Two major approaches to the 5-benzylic-1,3-thiazolidine-2,4-dione ring system have been reported, one of which is described in U.S. Pat. No. 4,572,912 (see, FIG. 2A). The other has been outlined more recently (see, Hulin B. et al., J. Med. Chem. 1992; 35(10): 1853–1864 and Wilson T. et al., J. Med. Chem. 1996; 39(3): 665–668).

Figure 2:
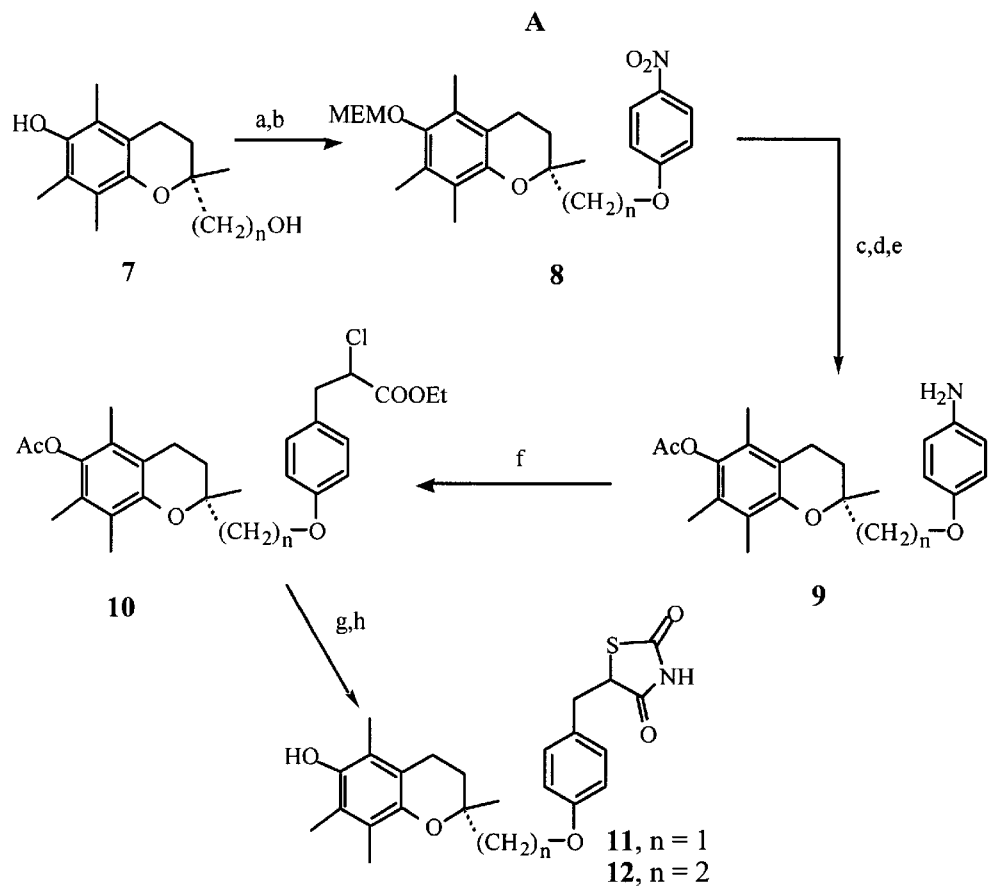
FIG. 2 Panel A illustrates a prior art synthesis scheme. Panel B illustrates an alternative synthesis scheme to generate intermediates of the present invention.
Figure 2:
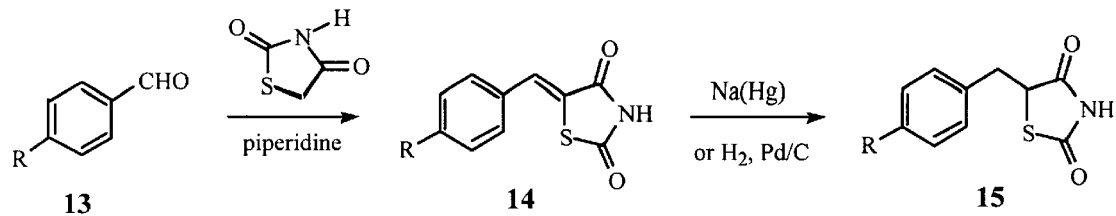

The approach outlined in FIG. 2A was cumbersome and thus researchers prepared euglycemic agents containing the thiazolidinedione ring system by exceptionally mild Aldol condensation of thiazolidinedione itself to a benzaldehyde 13 (see, FIG. 2B). The resultant arylidene thiazolidinediones 14 can then be reduced catalytically over Pd on C with hydrogen, or by the action of sodium-mercury amalgam to afford the desired ring systems 15. Not only is the approach outlined in FIG. 2B more direct than the earlier method, it employs milder condition thus avoiding potential side-reactions. For example, intermediate 9 has several aromatic C-H positions that are available for coupling to a diazonium intermediate during the aryl diazonium decomposition which leads ultimately to 10.

Figure 3:
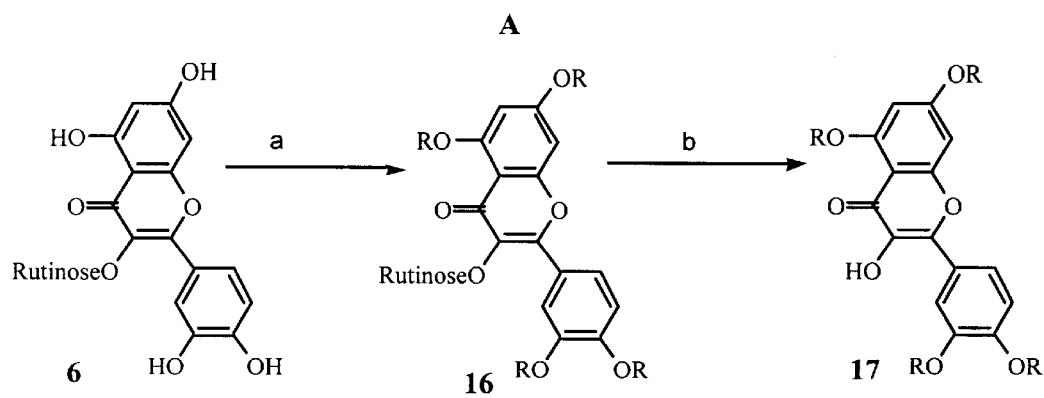
FIG. 3 Panel A illustrates selective alkylation of rutin. Panel B illustrates linkage of the flavone with thiazolidinedione.
Figure 3:
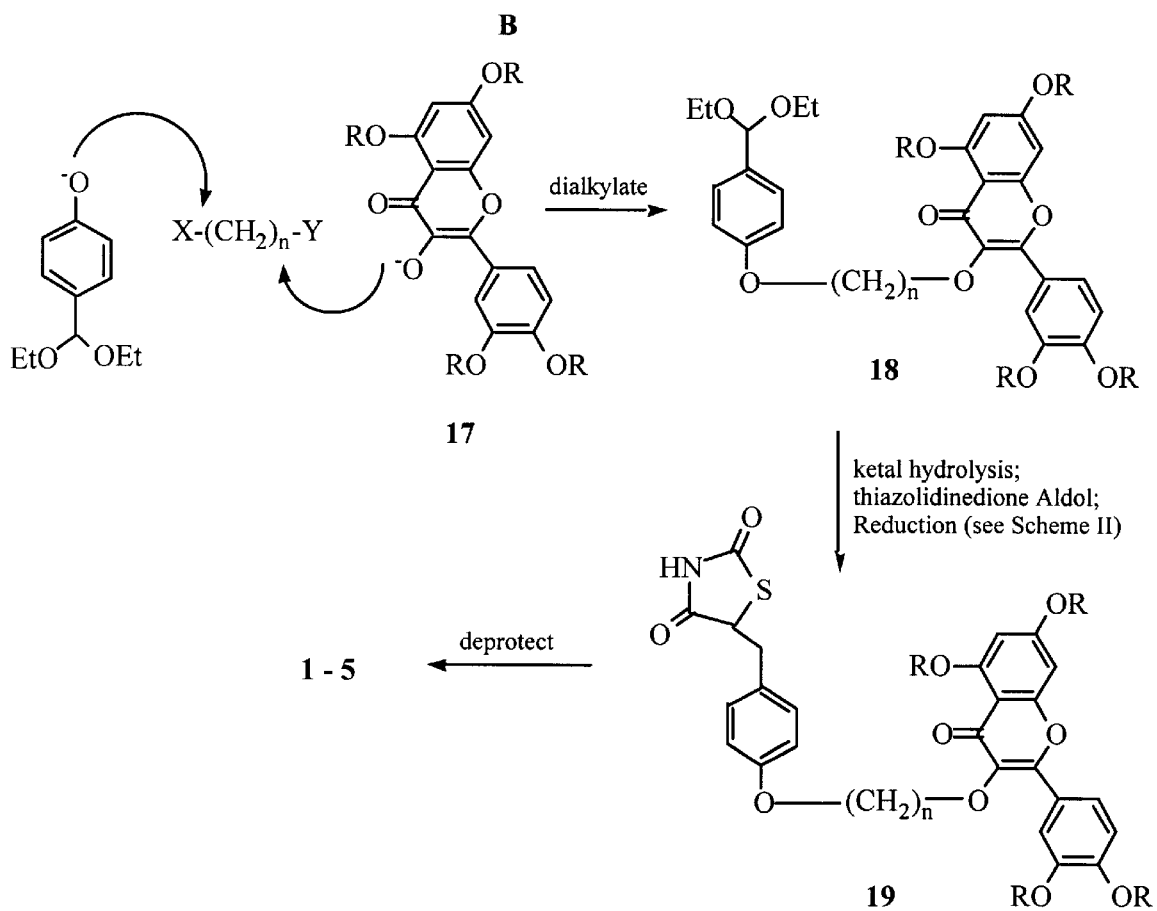

With reference to FIG. 3A, in order to alkylate the C-3 portion of the flavone moiety, it is possible to take advantage of the natural occupance of bioflavanoids such as rutin 6 (where R is a disaccharide), wherein C-3 is essentially already "blocked". The additional hydroxyl groups present on the C-3-sugar moiety do not present a problem because the hydroxy groups of a sugar are alcoholic, with $pK_a$ values in the range of 18, while the phenolic groups have $pK_a$ values as low as 9. Thus, a clear acidity difference makes selective deprotonation of the phenolic hydroxyls possible. Selective alkylation of rutin has been described previously as shown in FIG. 3A.

Preparation of the hydroxyethoxy derivative of quercitin is effected by phenoxide opening of ethylene oxide (see, He H. et al., *Yiyao Gongye* 1987; 18(5): 205–206). Thus, both rutin and chloroethanol react with sodium hydroxide. Rutin 6 gives the phenoxide anion, while chloroethanol undergoes intramolecular $S_N2$ reaction to afford oxirane (ethylene oxide). The phenoxide anion then opens the highly reactive oxirane to give 16 where R is $CH_2CH_2OH$. Removal of the disaccharide by acidic hydrolysis provides 17 (see, FIG. 3A). Application of this concept to rutin, with modification of the nature of the R groups in 17, has provided a clean route to the flavonoid portion of target compounds 1–5.

With reference to FIG. 3B, linkage of the flavone with the thiazolidinedione system proceeded as illustrated. After linkage gives the modified flavone 18, removal of the acetal protecting group, Aldol condensation and reduction provide the protected target compounds 19. Deprotection afforded the desired targets 1–5.

Figure 4:
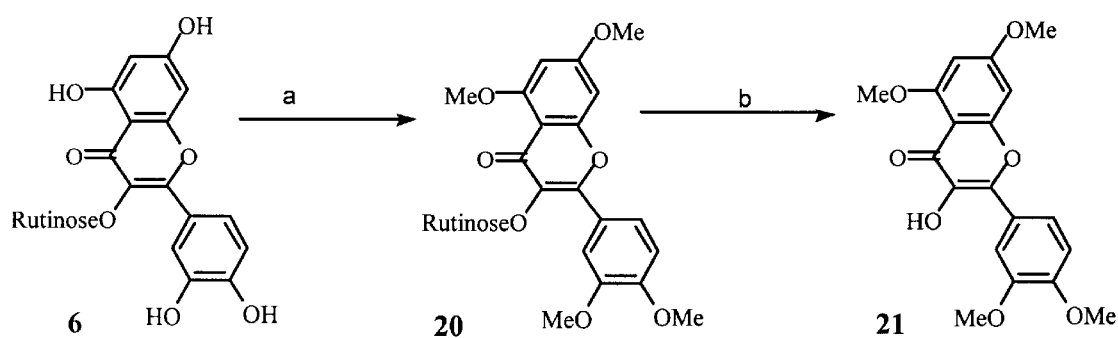
FIG. 4 illustrates a protection scheme for a flavone moiety.

With reference to FIG. 4, a straightforward protection scheme for the flavone system is illustrated which involves O-methylation of the phenolic groups. Tetramethylation of rutin 6 to furnish 20 is possible upon exposure of rutin to dimethylsulfate and sodium carbonate to give after mild acid-catalyzed hydrolysis, 3', 4', 5, 7-tetramethoxyflavone 21. Methyl protection was chosen because deprotection of anisoles to provide phenols has been studied extensively, and there are at least eighteen different removal methods reported in Green (see, Green T et al., *Protective Groups in Organic Synthesis*, 2nd ed. New York: John Wiley & Sons, Inc., 1991).

In one preferred embodiment, the present invention relates to compounds of Formula I, wherein Y is S; R is 3,4-dihydroxyphenyl; q is 1; n is 1 to 5; t is 0; m is 0; p is 0; z is 0; $R^1$ and $R^3$ are each hydroxy; and $R^2$ and $R^4$ are each hydrogen; (see, FIG. 1).

Figure 5:
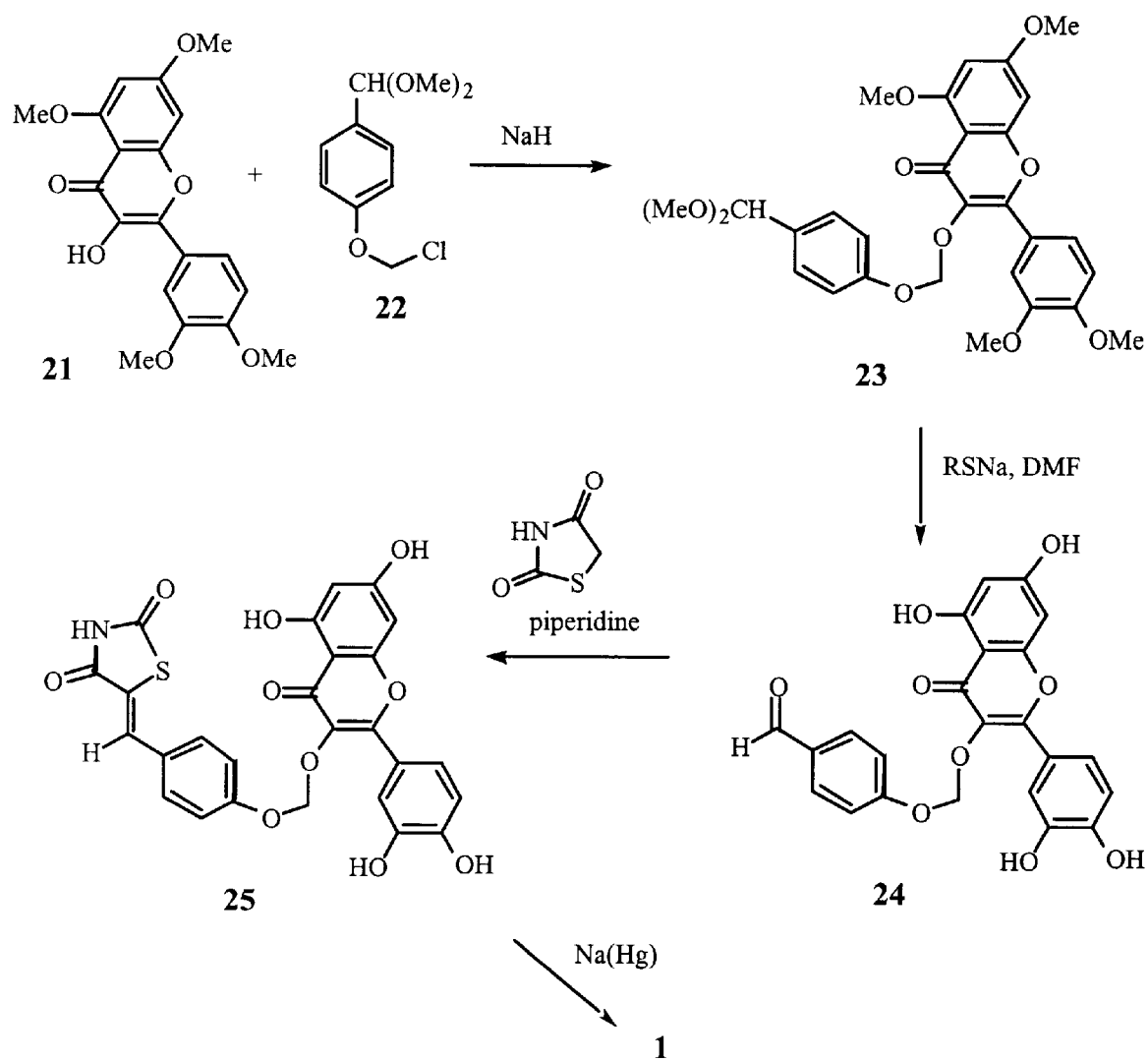
FIG. 5 illustrates a synthesis scheme for compounds of the present invention.

The synthesis of compounds of the foregoing embodiment is set forth in FIG. 5. As illustrated therein, treatment of 21 with base (e.g., NaH) followed by an appropriate chloromethyl ether sets in place the tethered species (23). Attack by an thioalkane anion of adequate steric bulk will allow for selective removal of the less hindered methyl moieties, and provide the phenolic aldehyde 24. If the acetal of the aromatic ring proves resistant to organo-sulfide anion, then a second mild acid hydrolysis step can be undertaken to arrive at 24. With the benzaldehyde in hand, its conversion to a thiazolidinedione follows readily, with mild Aldol-like condensation of thiazolidinedione itself with 24 will furnish 25. Reduction of 25, without an adverse effect on the chromanone ring system is likely under mild conditions previously employed with sodium-mercury amalgam. Several alternatives exist for this reduction, including, but not limited to, Pd/C. Thus, it is also possible to reduce 25 using catalytic hydrogenation over Pd/C. If this can be accomplished without reduction of the chromanone ring, then alternative protection schemes become available, such as benzyl protection.

Figure 6:
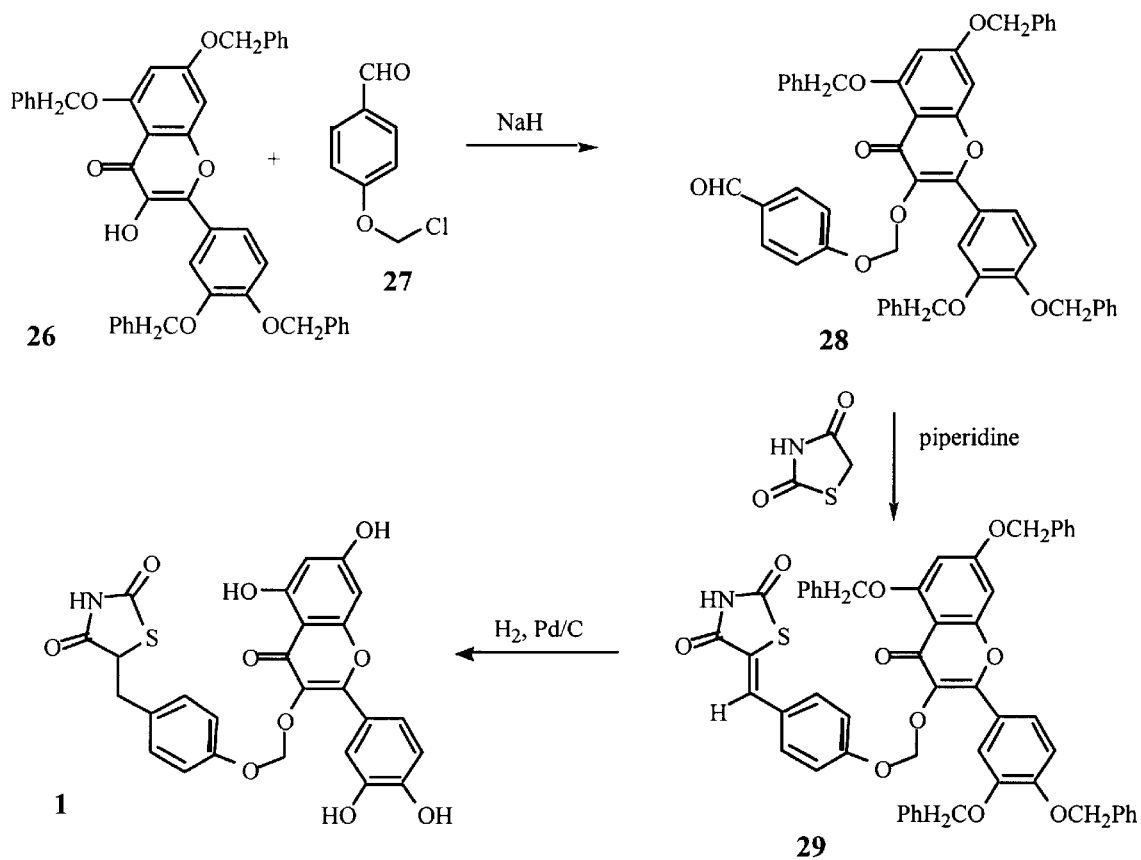
FIG. 6 Panel A illustrates a synthesis scheme for compounds of the present invention. Panel B illustrates acid hydrolysis of a compound of the present invention.
Figure 6:
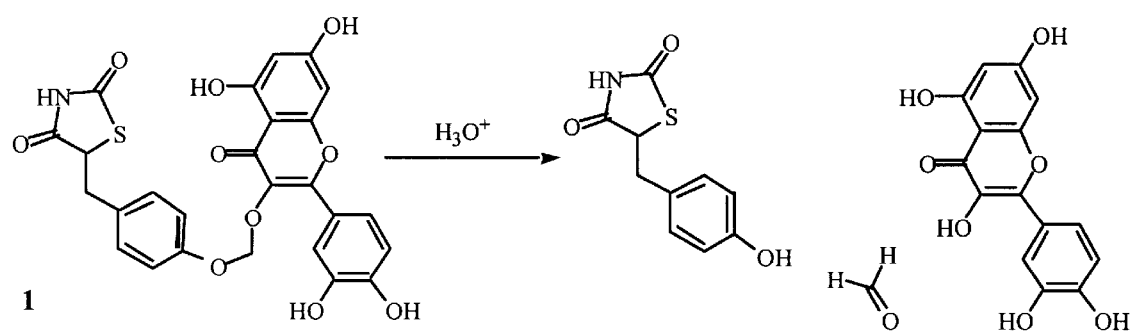

With reference to FIG. 6A, an alternative synthetic scheme to generate 1 is illustrated. As illustrated therein, a free aldehyde-chloromethyl ether (27) undergoes coupling to tetrabenzylquercetin 26. The benzaldehyde group is stable in these conditions as there is no enolizable (exchangeable) position in either molecule. After generation of 28, simple condensation to give the arylidene thiazolidinedione 29 will be straightforward. Reduction under catalytic conditions will provide the one carbon tether 1.

In another preferred embodiment, the present invention relates to compounds of Formula I, wherein Y is S; R is 3,4-dihydroxyphenyl; q is 1; n is 2; t is 0; m is 0; p is 0; z is 0; $R^1$ and $R^3$ are each hydroxy; and $R^2$ and $R^4$ are each hydrogen; (see, FIG. 7B).

Figure 7:
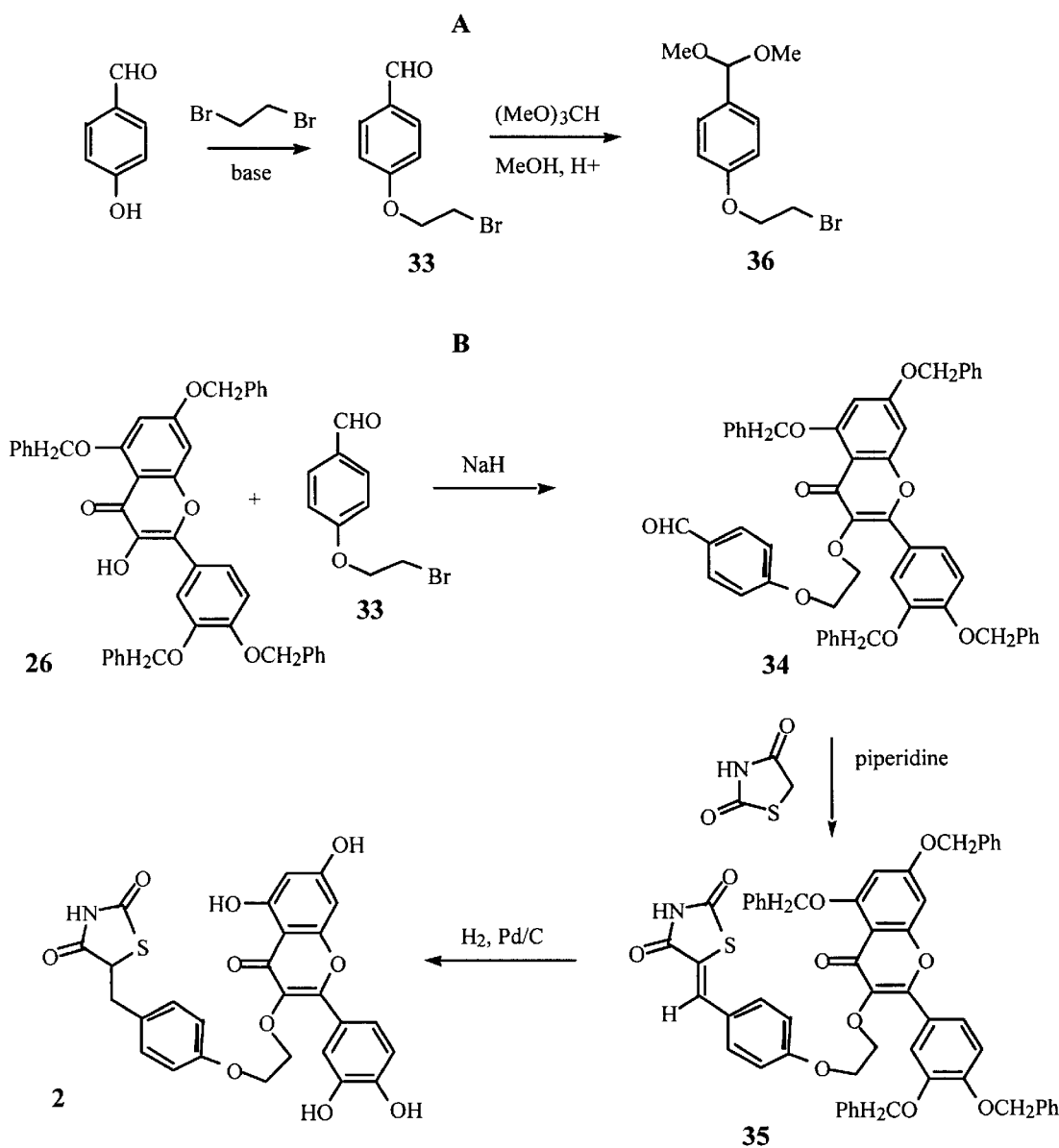
FIG. 7 Panel A illustrates a synthesis scheme for an intermediate compound of the present invention. Panel B illustrates a synthesis scheme for a compound of the present invention.

With reference to FIG. 7B, the synthesis of the two-carbon tether 2 is illustrated. The chemistry is similar to that used in the synthesis of 1, with some practical differences relating to various experimental details such as, reaction times and solvents, but also to the lack of aldehyde group protection. The O-alkylation of 33 will occur more slowly than the chloromethyl ether 27. However, the existence and the alkylation of aldehyde 33 with phenoxides has previously been described. (see, Nate H. et al., *Chem. Pharm. Bull.* 1987; 35(6): 2394–2411).

Alternatively, protection of the halo-benzaldehydes can be accomplished using methanol and trimethylorthoformate in the presence of a weak ammonium based acid. It is possible to modify the synthetic scheme outlined in FIG. 7B by utilizing acetal 36 (see, FIG. 7A) instead of 33. An additional step is added to deblock the ketal to arrive at 34. This synthesis is straightforward due to the presence of the para oxygen atom.

In another preferred embodiment, the present invention relates to compounds of Formula I, wherein Y is S; R is 3,4-dihydroxyphenyl; q is 1; n is 3–5; t is 0; m is 0; p is 0; z is 0; $R^1$ and $R^3$ are each hydroxy; and $R^2$ and $R^4$ are each hydrogen; (see, FIG. 1).

Figure 8:
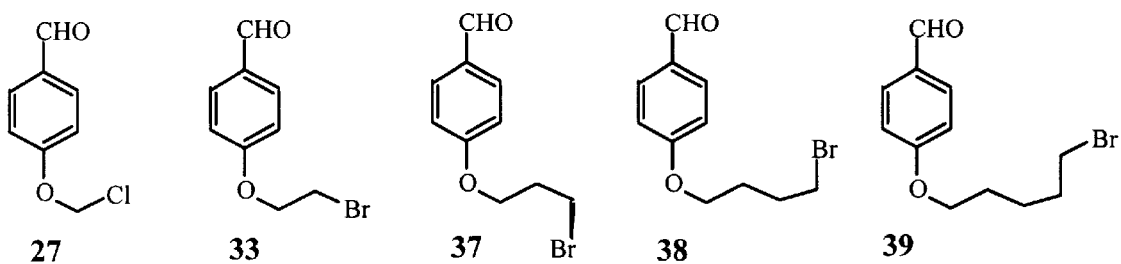
FIG. 8 Panel A illustrates intermediate compounds of the present invention. Panel B illustrates compounds of the present invention and intermediate compounds of the present invention.
Figure 8:
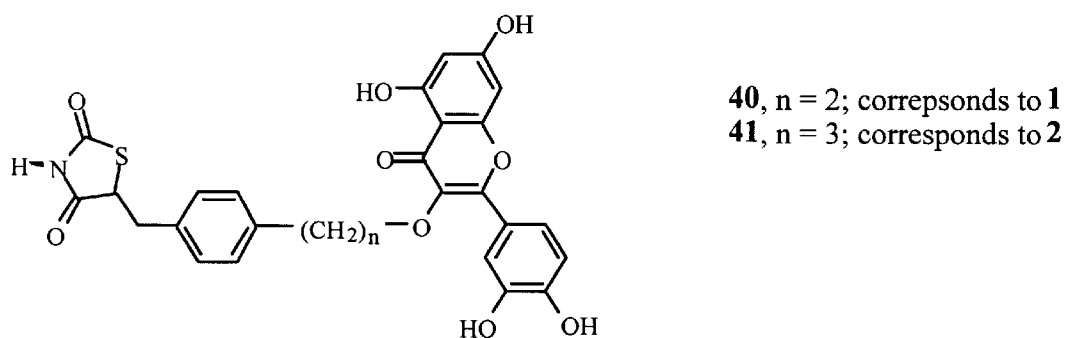
Figure 8:
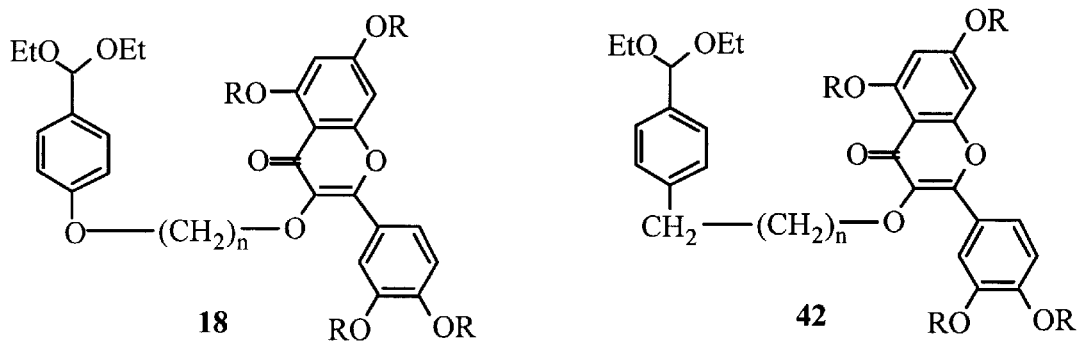

As illustrated in FIG. 8A, the reported benzaldehydes wherein n is 3–5 have been reported. For instance, aldehyde 27 has been described along with 33. The three-carbon side chain, 37, was prepared much in the same manner as the other bromides: i.e., alkylation of the dihaloalkane with the anion of p-hydroxybenzaldehyde (see, Schweizer E. et al.,*J. Org. Chem.* 1969; 34(1): 207–212). The four carbon aldehyde was prepared in 1989 by Ito S. (see, Japanese Patent No. 01,117,867). The ortho-analog of 39 was also prepared, (see, Nate H. et al., *Chem. Pharm. Bull.* 1987; 35(6): 2394–2411). Using these methods, the generation of benzaldehydes 37, 38 and 39 is possible. Using the same reaction sequence as illustrated in FIG. 7B, compounds 3, 4 and 5 can be made.

In yet another embodiment, the present invention relates to compounds of Formula I, wherein Y is O; R is 3,4-dihydroxyphenyl; n is 1 to 5 q is 0; t is 0; m is 0; p is 0; z is 0; $R^1$ and $R^3$ are each hydroxy; and $R^2$ and $R^4$ are each hydrogen; (see, FIG. 8B).

Figure 9:
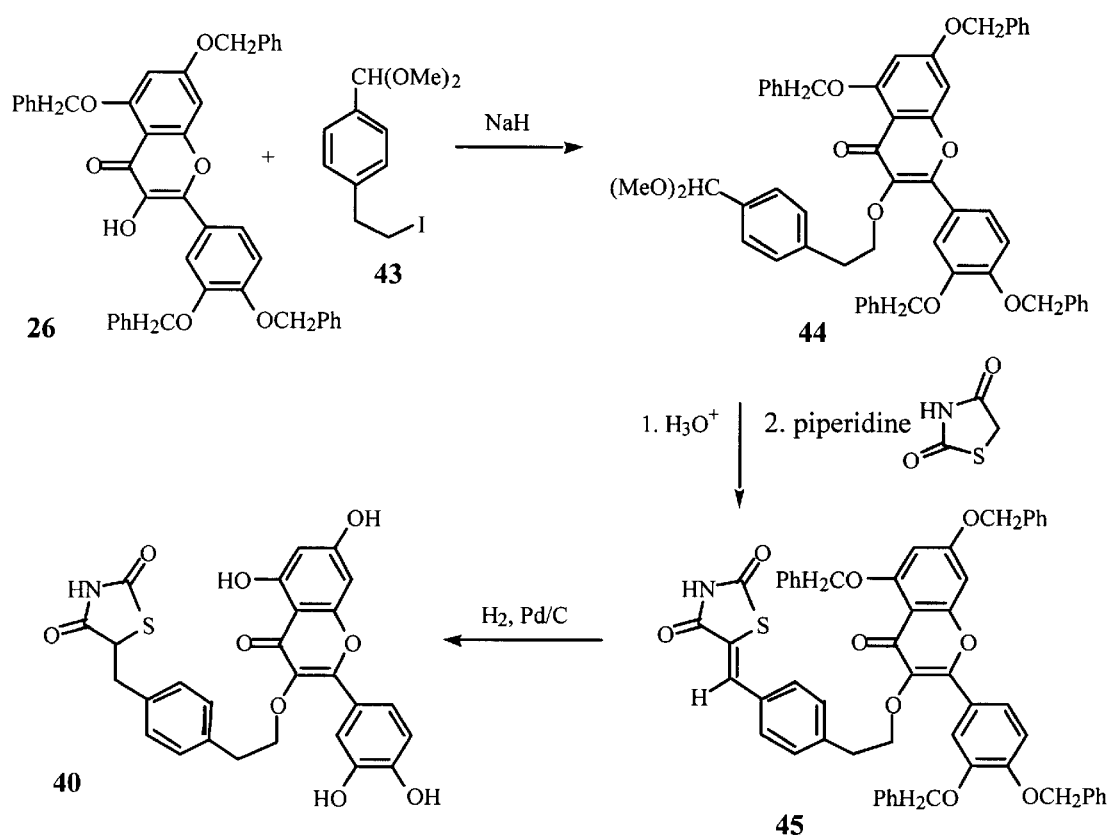
FIG. 9 illustrates a synthesis scheme for a compound of the present invention.

With reference to FIG. 8B, it is possible to synthesize versions of 1 by replacing one of the acetal oxygens with carbon, such as in structure 40 or 41. As shown in FIG. 9, compound 40 can be synthesized in a manner similar to that outlined previously. Alkylation of a 4-(2-haloethyl) benzaldehyde acetal such as in 43, with tetrabenzylquercetin 26 will lead to formation of the protected tether 44. Purification and deprotection of the aldehyde group with mild acid will provide an intermediate benzaldehyde, of structure similar to 28 or 34, which will then undergo Aldol-like condensation to give the arylidene thiazolidinedione 45. Finally, simultaneous double bond reduction and benzyl group deprotection will furnish the alternate target 40 (see, FIG. 9). It follows that homologous acetals can be used in this scheme to arrive at other tether lengths, and will provide structures such as 41 (see, FIG. 8B).

The addition of polar atoms in the tether could have several desirable effects including enhanced polarity for water solubility. As such, the present invention relates to compounds of Formula I, wherein R is 3,4-dihydroxyphenyl; q is 1; n is 2 t is 1; m is 2; p is 0; z is 0; $R^1$ and $R^3$ are each hydroxy; and $R^2$ and $R^4$ are each hydrogen. (see, FIG. 10A). In one embodiment, X is preferably oxygen.

An additional ethylene-glycol like unit can be added to 2 to furnish an analog resembling 5, the triether 47 (see, FIG. 10A). By minor modifications to the outlined schemes, it is possible to derive 47 from commercially available 2-bromoethyl ether ($BrCH_2CH_2OCH_2CH_2Br$) and the anion of para-hyroxybenzaldehyde. After generating adduct 46, coupling it to the tetrabenzyl ether 26 will proceed as expected to give the intermediate 47. The desired target 48 will become available as illustrated in FIG. 10A.

In addition, the present invention relates to compounds of Formula I, wherein R is 3,4-dihydroxyphenyl; q is 1; n is 2; X is $NR^6$, wherein $R^6$ a member selected from the group consisting hydrogen and optionally substituted ($C_1$–$C_6$) alkyl; t is 1; m is 2; p is 0; z is 0; $R^1$ and $R^3$ are each hydroxy; and $R^2$ and $R^4$ are each hydrogen. (see, FIG. 10B).

Figure 10:
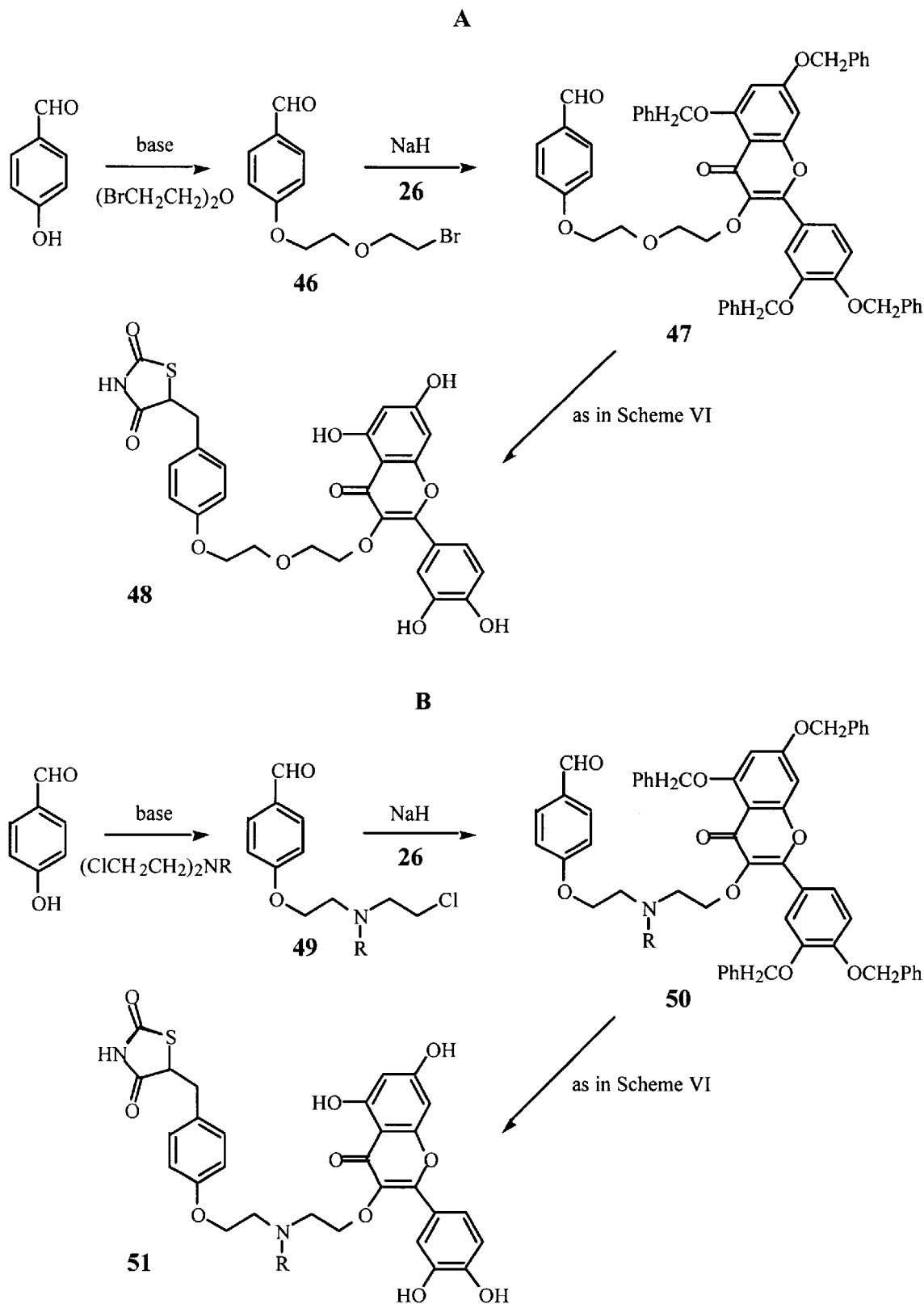
FIG. 10 Panel A illustrates a synthesis scheme for a compound of the present invention. Panel B illustrates a synthesis scheme for a compound of the present invention.

To generate these compounds, a simple modification to the scheme as shown in FIG. 10 is possible. The corresponding chloroethylamines are available and will work in place of bromethyl ether. With reference to FIG. 10B, reaction of the phenolic aldehyde with a weak base and nitrogen mustard will readily undergo rapid O-alkylation to give 49. This material is not expected to be stable under basic conditions thus it will be possible to add the anion of 26 directly to the reaction mixture to obtain 50 in a one-step operation. After generation of 50, following the scheme set forth in FIG. 5 will allow for conversion to target 51. It is also possible to engineer other atoms in this scheme such as X is S, S=O or $SO_2$, as well as longer tethering lengths and salt forms such as ammonium or sulfonium ions.

III. Thiazolidinedione Analogs

While the bulk of literature precedent exists for the thiazolidinediones as described above, it is possible to replace the sulfur moiety (Y is S) with another heteroatom such as oxygen i.e., Y is O. Oxazolidinediones are known to be pharmacologically similar to thiazolidinediones (see, Heitzmann, T. et al., *Arzneimittelforschung* 1995: 45(12), 1284–1288. and Turnbow, M. A. et al., *Endocrinology* 1995; 136(4), 1450–1458.) In addition, Y can be selenium, (Y is Se). (see, "Biochemistry of Selenium", by R. J. Shamberger, Plenum Press, pp 273–279 and Comrie et al., *J.Pharn. Pharacol.*, 16: 268–272 (1964)).

Figure 11:
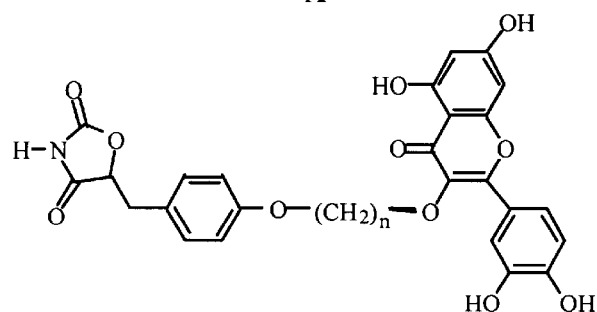
FIG. 11 Panel A illustrates compounds of the present invention. Panel B illustrates compounds of the present invention. Panel C illustrates compounds of the present invention.
Figure 11:
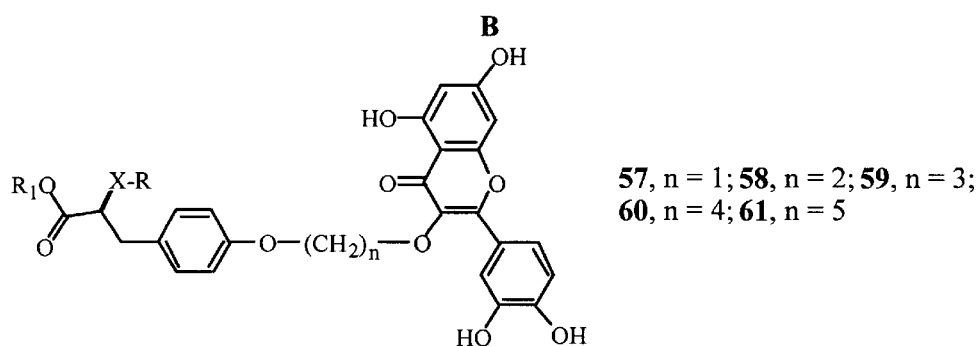
Figure 11:
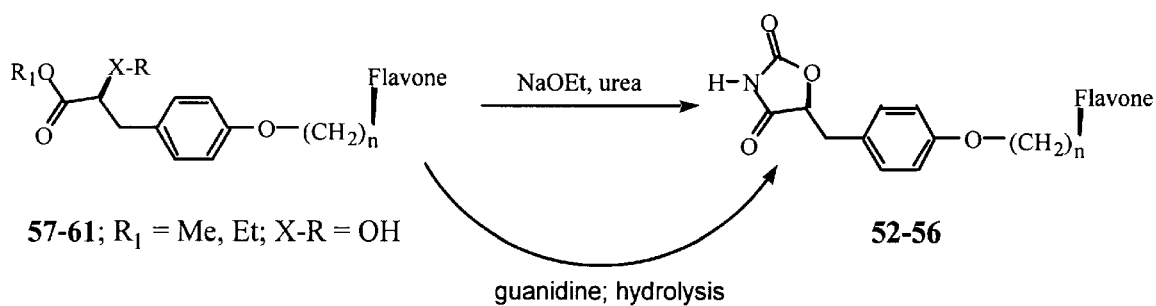

As such, in another embodiment, the present invention relates to compounds of Formula I wherein Y is O; R is H; q is 1; t is 0; n is 1 to 5; m is 0; p is 1; z is 0; $R^1$ and $R^3$ are each hydroxy; and $R^2$ and $R^4$ are each hydrogen (see, FIG. 11A). In this embodiment, the oxazolidinediones have the structures 52 through 56 (see, FIG. 11A), by analogy to the thiazolidinediones 1–5, and can in fact be accessed from another class of potential PPARγ agonists, the corresponding α-hydroxy, α-thioalkoxy or α-alkoxy carboxylic acids or carboxylate esters 57–61 (FIG. 11B).

While it is possible that the enantiomers of 52–56 might undergo epimerization in vivo, the corresponding acids and acid esters 57–61 will not be stereochemically labile. It is in fact possible to develop an enantiospecific route to the analogs 57–61, hence leading to enantiomerically pure 52–56.

Synthesis of 57–61, allows for production of the oxazolidinediones 52–56 by treatment with NaOEt and urea, or alternatively by condensation with guanidine followed by hydrolysis, thus providing for a convergent route to these analogs (see, FIG. 11C) (see, Lednicer, D. et al., Organic Chemistry of Drug Synthesis. John Wiley and Sons, Inc., N.Y., 1977. Chapter 5, pp 232–234.)

Figure 12:
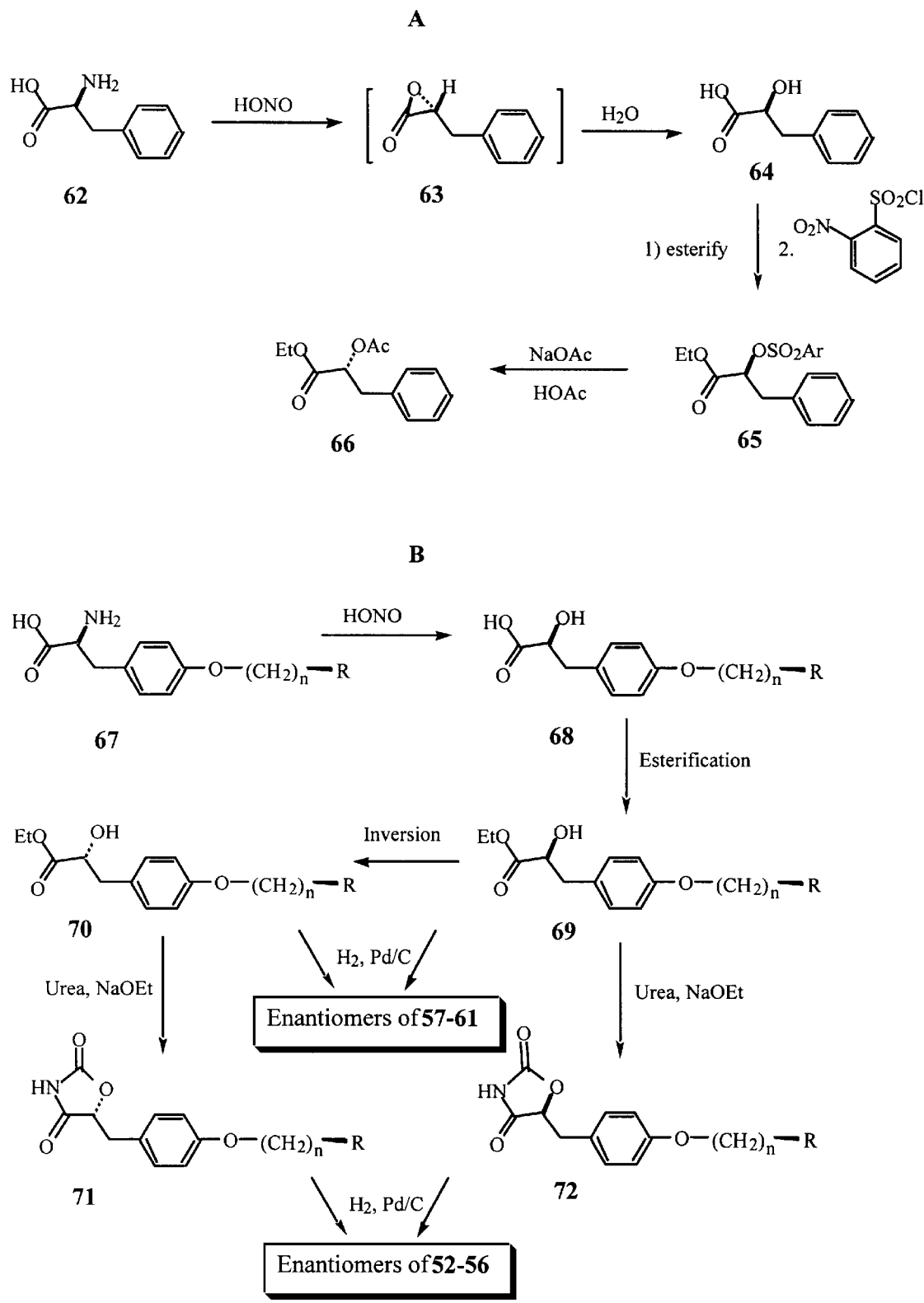
FIG. 12 Panel A illustrates intermediate compounds of the present invention. Panel B illustrates a synthetic scheme for compounds of the present invention.

The α-hydroxyacids corresponding to 57 –61 can be generated in chiral form by diazotization of an alkylated tyrosine. With reference to FIG. 12A, when phenylalanine 62 is reacted with nitrous acid the resultant α-hydroxyacid 64 retains the original stereochemistry as a consequence of a double inversion via intermediate 63. Further, the opposite stereoisomer 66 is obtained by a $S_N2$ reaction of a sulfonyl derivative 65 with acetate ion (see, Coppola, G. et al., Asymmetric Synthesis, Construction of Chiral Molecules Using Amino Acids. John Wiley and Sons, Inc., N.Y., 1987. Chapter 2.1, pp 45–46.)

With reference to FIG. 12B, diazotization can be carried out under basic conditions by reaction first with a alkyl nitrite to avoid ring nitrosation. The tethered amino acid 67 (wherein R is a protected flavone) will provide alcohol 68 which will be inverted to the other enantiomer as shown. Finally, either enantiomer of 68 will provide the oxazolidinediones 52–56. Thus, upon esterification of 68, ethyl ester 69 can then either be inverted as discussed above to furnish 70 or can itself be taken on to give the oxazolidinedione 72. Likewise, 70 can then also provide the enantiomeric oxazolidinedione 71. Deprotection of either as described above by hydrogenolysis will give the final products 52–56 in either enantiomer as desired.

The esters 70 or 69 will hydrogenolyzed directly to give the corresponding carboxylate alcohols 57 through 61. The ester can be left in place to serve as a prodrug, or will be removed by hydrolysis with base.

Figure 13:
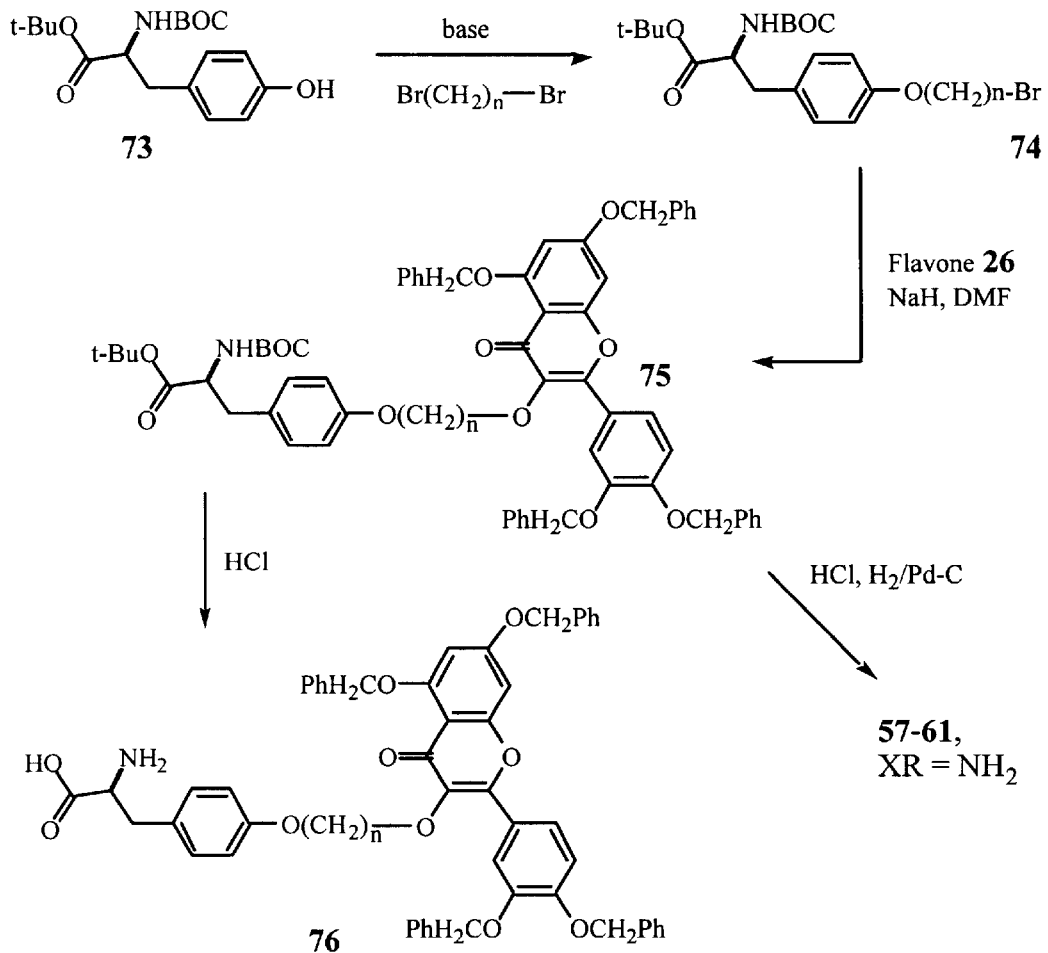
FIG. 13 Panel A illustrates compounds of the present invention. Panel B illustrates compounds of the present invention.
Figure 13:
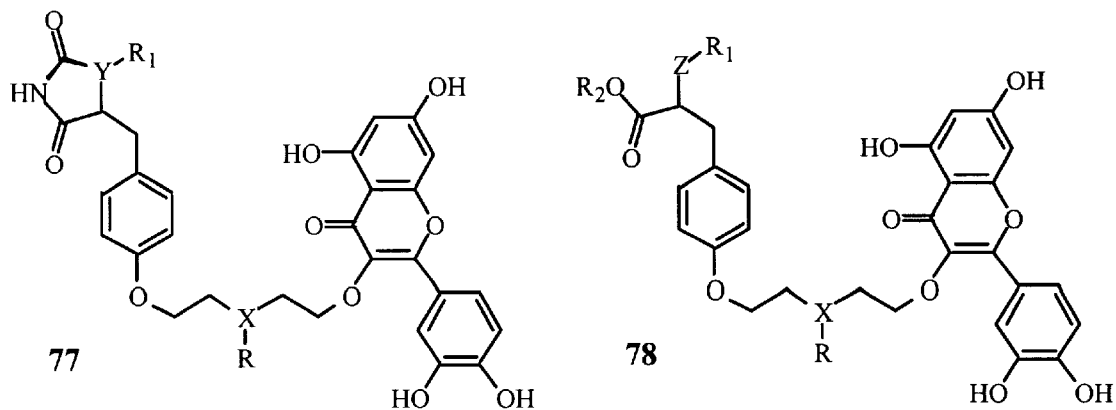

The tethered tyrosine derivative 67 will be accessible from a protected version of tyrosine commonly employed in peptide synthesis, i.e., N-tBOC-tyrosine tert-butyl ester 73 (see, FIG. 13A). Upon phenoxide formation of 73 and O-alkylation with the corresponding dihalide as outlined for the aldehydes 27, 33, and 37–39, formation of 74 will be evidenced. After coupling as described previously with the protected flavone, 26, a protected target 75 is accessible. To afford a final product directly, hydrogenolysis of 75 under acidic conditions will effect both benzyl group cleavage as well as BOC and t-Bu ester removal.

Alternatively, simple acid treatment will leave the flavonoid portion protected as 76 which will be diazotized (as in FIG. 12A) to obtain the X-R is OH series, thus providing access to 57–61 in both $NH_2$ and OH classes. Either 57 –61 with XR is OH or $NH_2$ will be used to generate the corresponding heterocycles such as the oxazolidinediones or even the imidazolinediones wherein XR is $NH_2$.

As was the case for the thiazolidinediones, the acids and oxazolidinediones can be linked via heteroatoms such as O, S or N. With reference to FIG. 13B, the preparation of targets such as 77 or 78 are synthesized utilizing chemistry outlined herein. In 77, Y can be O or N and $R_1$ in the case of O is an electron pair, but in the case of N can be any alkyl or aryl group or other functionality containing carbon compound. In 78, Z is O, N or S and in the cases of N and S, $R_1$ can be any alkyl or aryl group or other functionality containing carbon compound. The $R_2$ group can be a simple ester to promote bioavailability such as an ethyl ester which should be cleaved in vivo to the free acid ($R_2$ is H). In either of these structures, X is O, S or N and in the latter case, N would have an R group that could be any alkyl or aryl group or other functionality containing carbon compound.

IV. ALTERNATIVE FLAVANOIDS

Other antioxidants or natural products can be tethered by similar methods to the thiazolidinedione, oxazolidinedione or α-substituted carboxylic acids. Additional flavonoids which can be used according to the invention, include, but are not limited to, taxifolin, catechin, genistein, epicatechin, eriodictyol, naringenin, troxerutin, chrysin, tangeretin, luteolin, epigallocatechin and epigallocatechin gallate, fisetin, kaempferol, galangin, gallocatechin and epicatechin gallate.

Of particular interest are isoflavones including, but not limited to, genistein. In these cases the tether takes a different format. As such, in another embodiment, the present invention relates to compounds of Formula I, wherein R is H; q is 1; t is 1; n is 2; m is 2; p is 1; z is 0; $R^1$ and $R^3$ are each hydroxy; and $R^2$ and $R^4$ each hydrogen (see, FIG. 14A).

Figure 14:
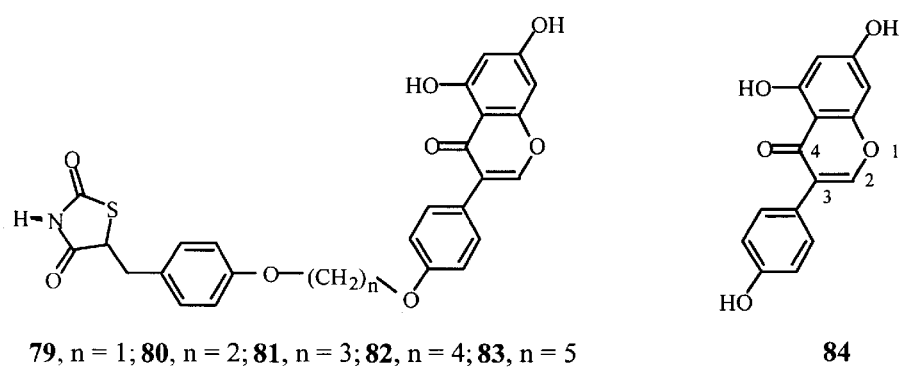
FIG. 14 Panel A illustrates compounds of the present invention. Panel B illustrates intermediate compounds of the present invention.
Figure 14:
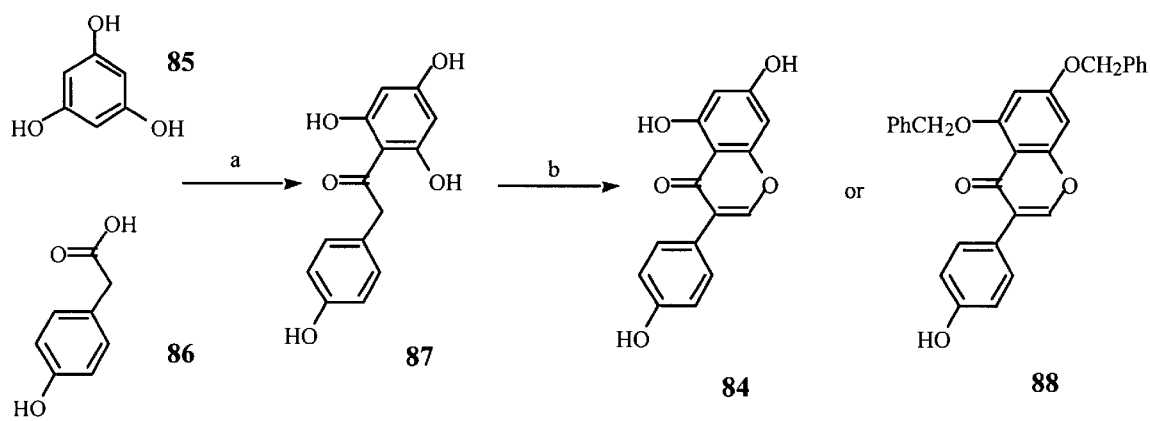

With reference to FIG. 14A, a normal alkyl chain attached to an oxygen atom already present in the isoflavone portion of the target compounds 79–83 requires no fundamental modification to the aromatic ring system. The antioxidant effects of the isoflavones are dependent upon the free phenolic oxygen atoms of the heterocyclic 4H-1-chromanone ring system. When the 4'-hydroxy group of genistein 6 is functionalized as in the targets 79–83, the antioxidant effect will be retained.

One approach to these compounds makes use of the methods outlined in FIG. 2B. Since the isoflavone ring system is synthesized in two steps from simple precursors, preparation of a protected version of 84, such as 88, by synthesis from simple precursors is possible. For example, Nair et al., Chang, Y. et al., *J. Agric. Food Chem.* 1994; 42: 1869–1871.) have shown that 4-hydroxyphenylacetic acid 86 can undergo a phenol acylation in a manner analogous to the Houben-Hoesch reaction using microwave radiation, but with vast improvement to yield and ease of synthesis, to provide genistein 84 as illustrated in FIG. 14B. Alternatively, an analogous one pot synthetic procedure has been published (see, T. Hase, et al., *J. Chem.Perk. Trans. I.* 3005, 1997).

With reference to FIG. 14B, an alternatively protected version of 84, namely 88, is possible by any number of pre-existing methods (see, Baker, W. et al., *J. Chem. Soc.* 1953; 1852–1862), or by starting with dibenzyloxyphenol instead of 85 and will be expected to provide 88 instead of 84. After the synthesis of the protected form of genistein 88, linkage gives the modified isoflavone 90, removal of the acetal protecting group, Aldol condensation and reduction will provide the protected target compounds 91. (see, FIG. 15) Deprotection will then afford the desired targets 79–83.

Figure 16:
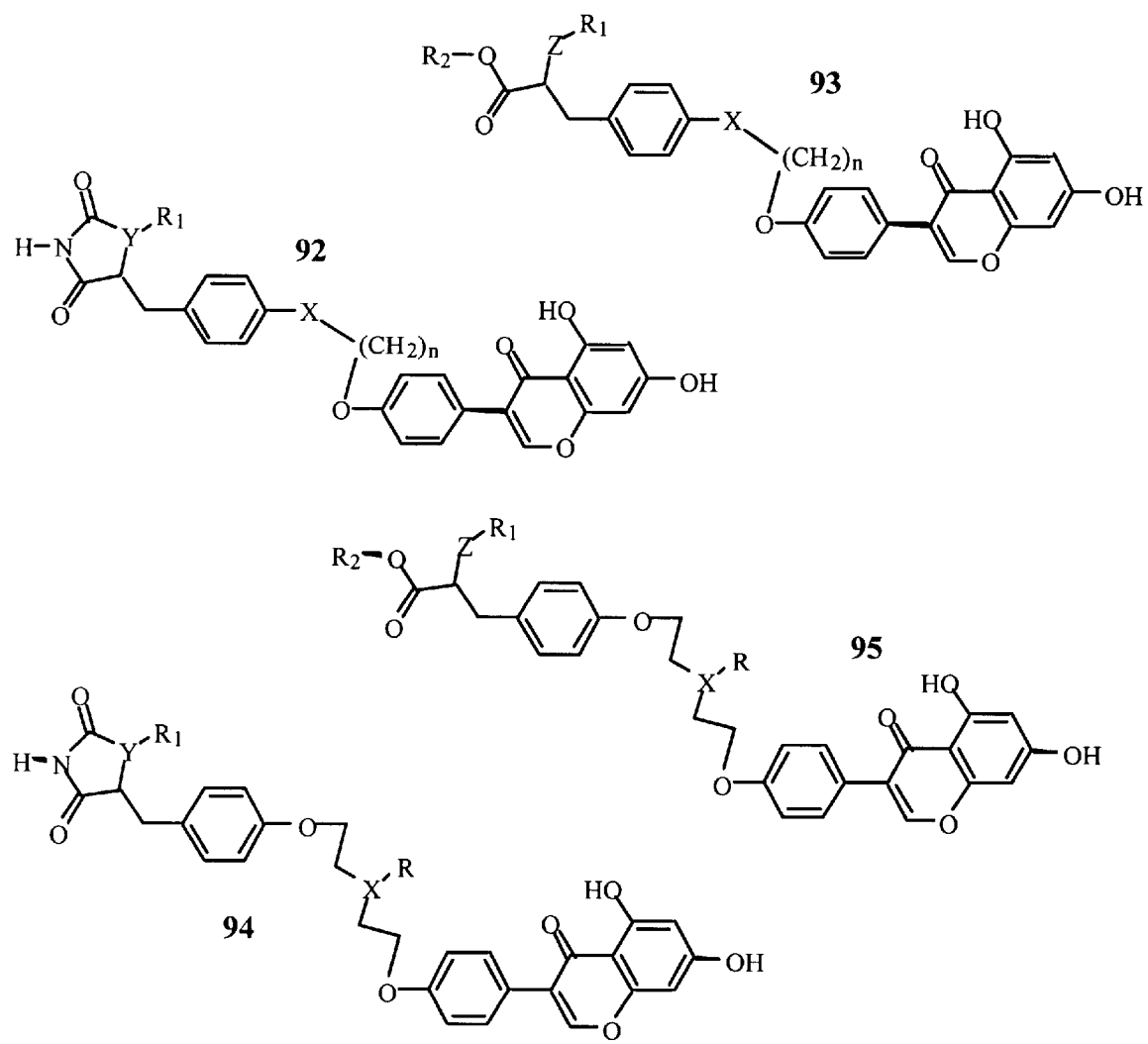
FIG. 16 illustrates compounds of the present invention.

With reference to FIG. 16, the tether attachment to the benzaldehyde ring can be via carbon or oxygen (92, 93) heteroatoms can be inserted into the tether itself to give hybrid structures such as 94 and/or 95 with head groups of either thiazolidinediones, oxazolidinediones, and α-substituted carboxylates or carboxylate derivatives such as esters or amides.

Additional flavonoids and isoflavanoids will be useful in practicing the present invention. As such, in another aspect, the present invention relates to compounds of Formula I wherein the isoflavonoid is represented by Formula II

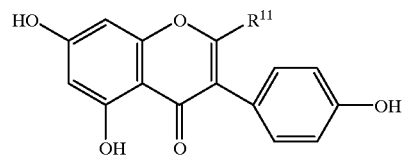

II wherein $R^{11}$ is a member selected from the group consisting of —A—$NR^{13}R^{14}$, —$CONHR^{15}$, —A—S—$R^{16}$ and —$COOR^{17}$, wherein A denotes a lower alkylene group; $R^{13}$ and $R^{14}$ are members independently selected from the group consisting of hydrogen, ($C_1$–$C_6$)alkyl, cycloalkyl and a sulfur- and a nitrogen-containing 5- or 6-membered heterocyclic ring, where the heterocyclic ring may be optionally substituted by one or two hydroxyl groups, or, alternatively, $R^{13}$ and $R^{14}$ together with the nitrogen to which they are bound form a pyrrolidine, piperidine or morpholine ring; $R^{15}$ is a member selected from the group consisting of hydrogen and optionally substituted ($C_1$–$C_6$)alkyl; $R^{16}$ is a member selected from the group consisting of ($C_1$–$C_6$)alkyl and a sulfur- and nitrogen containing 5- or 6-membered heterocyclic ring wherein said heterocyclic ring may be optionally substituted by one or two hydroxyl groups, carboxyl, or ($C_1$–$C_6$)alkoxycarbonyl groups; $R^{17}$ is optionally substituted ($C_1$–$C_6$)alkyl.

In one aspect, the modified isoflavone of Formula II will be used to generate a compound of Formula I, similarly as discussed above with 88, and then tethered as shown in FIG. 15. Removal of the acetal protecting group, Aldol condensation and reduction will provide the protected target compounds with the flavone being Formula II (see, FIG. 15). Deprotection will then afford the desired target of Formula I having an flavone moiety of Formula II.

Figure 15:
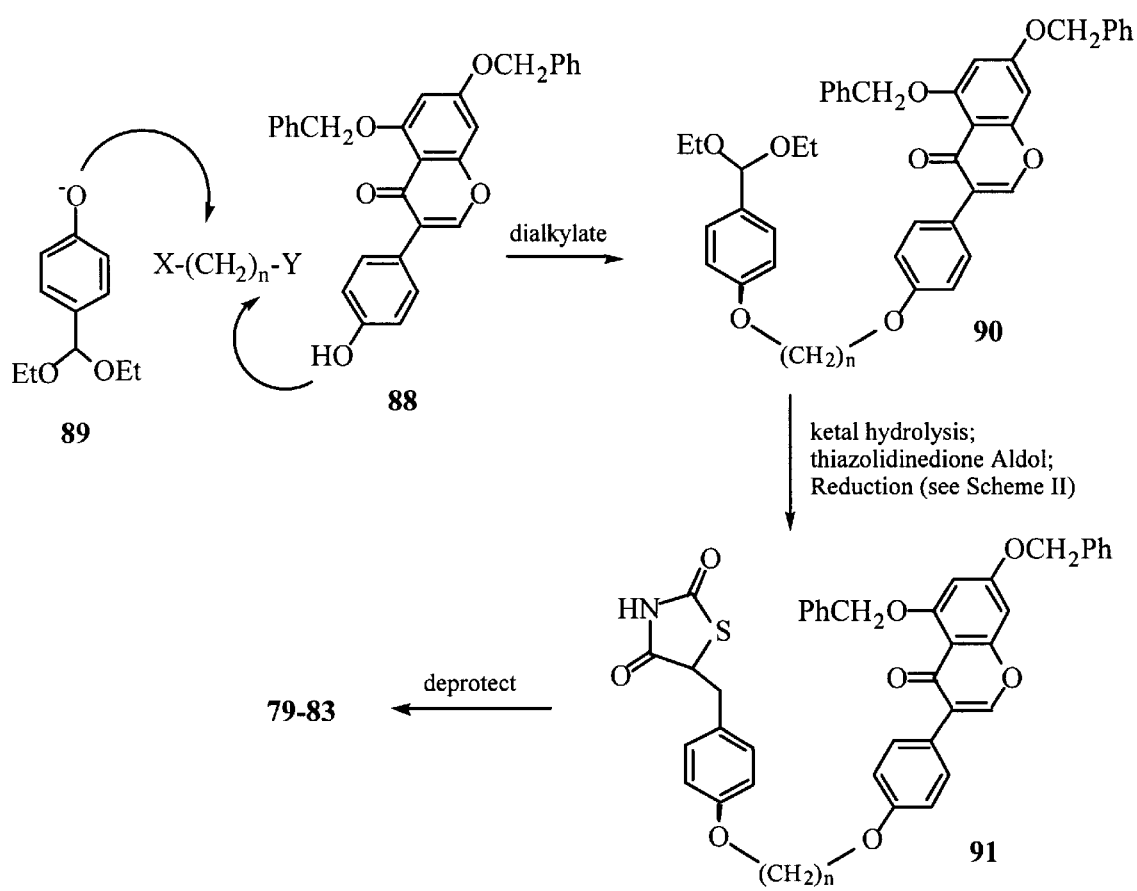
FIG. 15 illustrates a synthesis scheme for compounds of the present invention.

Although the attachment of thiazolidinedione moiety to the isoflavone of Formula II is preferably as outlined in FIG. 15, those of skill in the art will appreciate that the synthetic schemes can be modified to accommodate various functionality at $R^{11}$. For instance, when $R^{11}$ is —$CONHR^{15}$, and $R^{15}$ is hydrogen, the amino group will need to be protected and deprotected to generate the compound of Formula I. Various protection groups are available for amino groups such as carbamates and amides. (see, Green T et al., *Protective Groups in Organic Synthesis*, 2nd ed. New York: John Wiley & Sons, Inc., 1991).

Isoflavones of Formula II and their synthesis are described in detail in U.S. Pat. No. 4,841,077. Briefly, for compounds having the radical —A—$NR^{13}R^{14}$, a 2-methylisoflavone derivative is brominated using N-bromosuccinimide in carbon tetrachloride to generate the 2-bromo-methylisoflavone and subsequent reaction with various amines with the 2-bromo-methylisoflavone. The carboxamide compounds represented by Formula II wherein —$CONHR^{15}$ can be prepared by reaction of ammonia or an amine with a carboxylic acid derivative of an isoflavone. The substituted thio-lower-alkyl-isoflavone derivatives represented by Formula II wherein —A—S—$R^{16}$, can be prepared by reaction of a halogeno-lower-alkyl-isoflavone derivative with a thiol or an alkali metal salt thereof. The compounds represented by Formula II wherein —$COOR^{17}$ can be prepared by esterification or ester exchange reaction between a carboxylic acid, a salt, an ester or a reactive derivative thereof with a substituted or unsubstituted alkanol of or a reactive derivative thereof.

Flavone derivatives of Formula II can prepared by cyclization reactions. Of various types of cyclization reaction of a 2,4,6-trihydroxy α-phenyl-acetophenone derivative with an acid halide or acid anhydride to form an isoflavone derivative is the most preferred because the substituent at position 2 can be simultaneously introduced.

In yet another aspect, this invention relates to compounds of Formula I wherein the flavonoid moiety is represented by Formula III

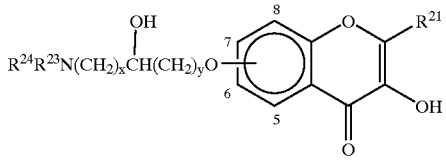

III wherein $R^{21}$ is 3,4 dihydroxyphenyl; $R^{23}$ is hydrogen or optionally substituted $(C_1-C_6)$alkyl; $R^{24}$ is phenyl, benzyl or $R^{25}(CH_2)_sCH(T)(CH_2)_k$, or a heterocyclic ring having the formula

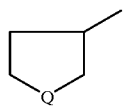

or alternatively, together with $R^{23}$ and the nitrogen atom to which they are bound form a 5- or 6-membered heterocyclic ring having the formula

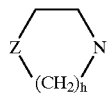

$R^{25}$ is either phenoxy or unsubstituted, monosubstituted, or disubstituted Ar, wherein, Ar is a member selected from the group consisting of phenyl, pyridinyl, furanyl, thiophenyl, naphthyl, each substituent of monosubstituted Ar is a member selected from the group consisting of hydroxy, $(C_1-C_6)$ alkoxy, and $O(CH_2)_rCO_2R_{23}$, each substituent of disubstituted Ar is independently hydroxy or $(C_1-C_6)$alkoxy; Q is a member selected from the group consisting of $SO_2$, S, or O; x is an integer from 1 to 5; y is an integer from 1 to 5; h is an integer from 1 to 2; k is an integer from 1 to 7; r is an integer from 1 to 2; s is a integer from 0 to 6; T is either hydrogen or OH; Z is a member of the group consisting of $CH_2$, O, NH, $NCH_3$, and

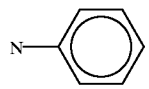

q is an integer from 0 to 1; n is an integer from 0 to 5; t is an integer from 0 to 1; m is an integer from 0 to 2; p is an integer from 0 to 1; z is an integer from 0 to 1; provided that (1) at least one of x and y is one and (2) s plus k total no more than 7.

The synthesis of flavones of Formula III are described in detail in U.S. Pat. No. 4,889,941. Briefly, these compounds can be generated by reacting a flavone compound with a ω-haloolefin in the presence of a base such as sodium or potassium hydroxide, potassium carbonate, or piperidine, and a solvent such as an alcohol of 1–4 carbon atoms, acetone, dimethylformamide, or dimethylsulfoxide, to give a flavone olefin. This flavone olefin is allowed to react with peroxides such as m-chloroperbenzoic acid or peracetic acid in a suitable solvent such as chloroform, methylene chloride or acetic acid, to produce an epoxide. Treatment of this epoxide with various amines in an alcoholic solvent of 1–4 carbons at a suitable temperature, or in the presence of a Lewis acid such as triethylaluminum in methylene chloride yields a product of Formula III.

Preferably, compounds of Formula III will be used to generate compounds of Formula I using the procedures similar to those illustrated in FIG. 5, wherein the attachment of thiazolidinedione moiety to the flavone of Formula III is via the hydroxyl group at C-3. Those of skill in the art will appreciate that the synthetic schemes as previously outlined can be modified to accommodate various side-chain functionalities at $R^{23}$ and $R^{24}$. Protective groups will be required at reactive sites to temporarily block their reactivity. These groups will then be removed to generate the compounds of Formula I after the coupling of the thiazolidinedione moiety to the flavone of Formula III.

In another aspect, this invention relates to compounds of Formula I wherein the flavone is represented by Formula IV

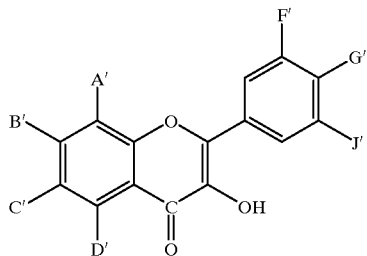

IV in which: A', C' and D', independently of one another, represent H, OH or $OCH_3$; B', F', G' and J', independently of one another, represent H, OH, $OCH_3$ or —$OCH_2$—$CH_2$— OH, with the proviso that at least two of the radicals A' to G' or J' represent OH. The compounds of formula IV are known (see, U.S. Pat. No. 4,431,912). They can be obtained in particular according to the processes described in "The Flavonoids", Harborne J. B., Mabry T. J., Helga Mabry, 1975, pages 1 to 45.

Preferably, compounds of Formula IV will be used to generate compounds of Formula I using the procedures similar to those illustrated in FIG. 5, wherein the attachment of thiazolidinedione moiety to the flavone of Formula IV is via the hydroxyl group at C-3. Those of skill in the art will appreciate that the synthetic schemes as previously outlined can be modified to accommodate various side-chain functionalities. Protective groups will be required at reactive sites to temporarily block their reactivity. These groups will then be removed to generate the compounds of Formula I after the coupling of the thiazolidinedione moiety to the flavone of Formula IV.

In still yet another aspect, this invention relates to compounds of Formula I wherein the flavonoid is represented by Formula V

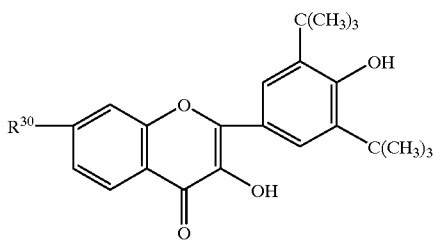

in which $R^{30}$ represents: a hydrogen or a radical $OR'^{30}$ in which $R'^{30}$ represents:

a) hydrogen or b) an alkyl radical containing from 1 to 10 carbon atoms in a straight or branched chain optionally substituted by one or more substituents selected from the group consisting of:
  i) phenyl and monocyclic or bicyclic aromatic heterocyclic radicals, all optionally substituted by one ore more substituents selected from halogen atoms, such as chlorine, bromine or fluorine and trifluoromethyl and hydroxy radicals and alkyl and alkoxy radicals each having from 1 to 5 carbons atoms in a straight or branched chain;
  ii) carboxy;
  iii) alkoxycarbonyl in which the alkoxy group contains from 1 to 5 carbons atoms in a straight or branched chain;
  iv) aminocarbonyl of the formula: —$C(O)NR'^{31}$ and $R'^{32}$ in which each of $R'^{31}$ and $R'^{32}$ which may be identical or different, represent: a hydrogen atom, or an alkyl radical having from 1 to 5 carbon atoms in a straight or branched chain, or $R'^{31}$ and $R'^{32}$ form together with the nitrogen atom to which they are bonded a heterocyclic radical optionally containing a second hetero atom selected from oxygen, nitrogen and sulfur, which heterocyclic radical may be substituted by an alkyl radical having from 1 to 5 carbon atoms in a straight or branched chain or by an aralkyl radical, such as, for example, a benzyl radical, the aryl moiety of which is optionally substituted by one or more alkyl and alkoxy radicals each having from 1 to 5 carbon atoms in a straight or branched chain;
  v) an amino radical of the formula —$C(O)NR''^{31}R''^{32}$ in which each of $R''^{31}$ and $R''^{32}$ may be identical or different, represents: hydrogen, or alkyl or hydroxyalkyl each having from 1 to 5 carbon atoms in a straight or branched chain, or $R''^{31}$ and $R''^{32}$ form together with the nitrogen atom to which they are bonded a heterocycle optionally containing another heteroatom: oxygen, nitrogen or sulfur,
  vi) a radical —OR" in which R" represents hydrogen, an alkyl radical having from 1 to 5 carbon atoms in a straight or branched chain or a group —COA in which: A represents an alkyl radical having from 1 to 5 carbon atoms in a straight or branched chain, or a radical —$C(O)NR''^{31}$ and $R''^{32}$ in which $R''^{31}$ and $R''^{32}$ are as defined above, and
  vii) $SO_3H$ and $SO_3M$ in which M represents an alkali metal.
c) an acyl radical of the formula: —$COR'''^{30}$ in which $R'''^{30}$ represents: an alkyl radical having from 1 to 10 carbon atoms in a straight or branched chain, an aralkyl radical, the aryl moiety of which is optionally substituted by one or more substituents selected from halogen atoms and hydroxy radicals and alkyl and alkoxy radicals each having from 1 to 5 carbon atoms in a straight or branched chain, or an aryl radical optionally substituted in the same manner as the aryl moiety of the aralkyl radical defined above, and d) tosyl. In addition, their steroisomers and also their possible addition salts with a pharmaceutically acceptable acid or base.

The synthesis of flavones of Formula V are described in detail in U.S. Pat. No. 5,280,024. The synthesis of compounds of Formula V is accomplished by condensing a phosphorane and a benzoic acid chloride. The reaction of the phosphorane and benzoic acid chloride is carried out in an especially suitable manner by operating in a suitable solvent, such as, for example, pyridine or a mixture of toluene and pyridine, while heating under reflux for approximately three hours.

Preferably, compounds of Formula V will be used to generate compounds of Formula I using the procedures similar to those illustrated in FIG. 5, wherein the attachment of thiazolidinedione moiety to the flavone of Formula V is via the hydroxyl group at C-3. Those of skill in the art will appreciate that the synthetic schemes as previously outlined can be modified to accommodate various side-chain functionalities. Protective groups will be required at reactive sites to temporarily block their reactivity. These groups will then be removed to generate the compounds of Formula I after the coupling of the thiazolidinedione moiety to the flavone of Formula V.

In other aspects, this invention relates to compounds of Formula I wherein the flavonoid is represented by Formula VI

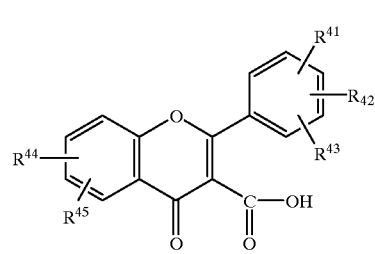

wherein: $R^{41}$ represents hydrogen, lower alkyl, halogen, hydroxy, lower alkylcarbonyloxy or an $R^{49}$ —O group; where $R^{49}$ represents an alkyl or alkenyl group with up to 20 carbon atoms; $R^{42}$ represents hydrogen, lower alkyl, halogen, hydroxy, lower alkylcarbonyloxy or an $R^{49}$ —O group, wherein $R^{49}$ has the above meaning, and $R^{43}$ represents hydrogen, lower alkyl, halogen, hydroxy, lower alkylcarbonyloxy or an $R^{49}$ —O group, wherein $R^{49}$ has the above meaning, or two of the substituent groups $R^{41}$ to $R^{43}$ are bonded to adjacent carbon atoms and together represent an alkylenedioxy group with 1 or 2 carbon atoms, with the proviso that if more than one of the substituent groups $R^{41}$ to $R^{43}$ represent oxygen-containing groups, these groups are identical; $R^{44}$ represents hydrogen, lower alkyl, halogen, hydroxy, lower alkylcarbonyloxy or an $R^{49}$ —O group, wherein $R^{49}$ has the above meaning, and $R^{45}$ represents hydrogen, lower alkyl, halogen, hydroxy, lower alkylcarbonyloxy or an $R^{49}$ —O group, wherein $R^{49}$ has the above meaning, or $R^{44}$ and $R^{45}$ are bonded to adjacent carbon atoms and together form an alkylenedioxy group with 1 or 2 carbon atoms, with the proviso that if both $R^{44}$ and $R^{45}$ represent oxygen-containing groups, these groups are identical, and, if $R^{41}$, $R^{42}$ or $R^{43}$ represent hydroxy or lower alkylcarbonyloxy groups, oxygen-containing groups $R^{44}$ and $R^{45}$ are identical to these groups.

The synthesis of flavones of Formula VI are described in detail in U.S. Pat. No. 4,886,806. Compounds of Formula VI will be used to generate compounds of Formula I using the procedures illustrated in FIG. 5 above. Briefly, the flavones of Formula VIII are prepared by first lithiating the 3-position of a flavone by reacting the flavone with nucleophile-free organic lithium base and by treating the lithiated intermediate product with carbon dioxide, whereby the lithium is then replaced by the carboxyl group. In particular, preferably lithium diisopropylamide or also lithium tetramethylpiperidide or lithium hexamethyldisilazide are organic lithium bases suitable as lithiating agents. The lithiation is carried out in a solvent which is inert under the reaction conditions, for instance a cyclic ether such as tetrahydrofuran, at temperatures between −90° C. and −50° C. The resulting 3-lithio-flavone compounds are processed further directly into the acids by treating the reaction solution with carbon dioxide and then acidifying it.

Preferably, compounds of Formula VI will be used to generate compounds of Formula I using the procedures similar to those illustrated in FIG. 5, wherein the attachment of thiazolidinedione moiety to the flavone of Formula V is via the carboxyl group at C-3. Those of skill in the art will appreciate that the synthetic schemes as previously outlined can be modified to accommodate various side-chain functionalities. Protective groups will be required at reactive sites to temporarily block their reactivity. These groups will then be removed to generate the compounds of Formula I after the coupling of the thiazolidinedione moiety to the flavone of Formula VI.

Preferred compounds of Formula I are set forth in Table I below.

tained by high performance liquid chromatography. A variety of columns (normal phase silica gel, reverse phase C-18, etc.) are available, as are computer workstations to analyze the results. Once reaction products are deemed greater than 99.5% HPLC pure, they can be analyzed by elemental analysis, NMR spectroscopy, FTIR, UV and EI or CI mass spectroscopy. Exact mass determinations will be possible and particularly applicable to intermediates. Other physical properties can be determined and recorded such as solubility, melting point, stability, etc. A careful study of chemical stability can be performed and suitable formulation for the oral route of administration can be examined.

VI. BIOLOGICAL ASSAY

Compounds of Formula I are activators of PPARγ. As described hereinbelow, a transient cotransfection assay can be used to screen for PPARγ antagonist. In this assay, chimeras are constructed that fuse the ligand binding domains of three murine PPAR subtypes (α,γ and NUC-1) to the DNA binding domain of the yeast transcription factor GAL4. Expression plasmids for the GAL4-PPAR chimeras are then transfected into CV-1 cells with a reported construct containing five copies of the GAL4 DNA binding site upstream of the thymidine kinase (tk) promoter driving chloramphenicol acetyl transferase (CAT) gene expression. Using this assay systems, compounds of Formula I which are activators of PPARγ and not PPARα and NUC-1 are identified. (see, J. M. Lehmann et al., *J. Biol. Chem.* 270:12953–12956 (1995)).

Plasmids—GAL4-PPAR chimera expression constructs contain the translation initiation sequence and amino acids

TABLE I

| cmp # | Y | q | n | X | t | m | p | z | R | R$^1$ | R$^2$ | R$^3$ | R$^4$ |
|---|---|---|---|---|---|---|---|---|---|---|---|---|---|
| 1 | S | 1 | 1 | — | 0 | 0 | 0 | 0 | 3,4 di-hydroxyphenyl | OH | H | OH | H |
| 2 | S | 1 | 2 | — | 0 | 0 | 0 | 0 | 3,4 di-hydroxyphenyl | OH | H | OH | H |
| 3 | S | 1 | 3 | — | 0 | 0 | 0 | 0 | 3,4 di-hydroxyphenyl | OH | H | OH | H |
| 4 | S | 1 | 4 | — | 0 | 0 | 0 | 0 | 3,4 di-hydroxyphenyl | OH | H | OH | H |
| 5 | S | 1 | 5 | — | 0 | 0 | 0 | 0 | 3,4 di-hydroxyphenyl | OH | H | OH | H |
| 40 | S | 0 | 2 | — | 0 | 0 | 0 | 0 | 3,4 di-hydroxyphenyl | OH | H | OH | H |
| 41 | S | 0 | 3 | — | 0 | 0 | 0 | 0 | 3,4 di-hydroxyphenyl | OH | H | OH | H |
| 48 | S | 1 | 2 | O | 1 | 2 | 0 | 0 | 3,4 di-hydroxyphenyl | OH | H | OH | H |
| 51 | S | 1 | 2 | N-ethyl | 1 | 2 | 0 | 0 | 3,4 di-hydroxyphenyl | OH | H | OH | H |
| 52 | O | 1 | 1 | — | 0 | 0 | 0 | 0 | 3,4 di-hydroxyphenyl | OH | H | OH | H |
| 53 | O | 1 | 2 | — | 0 | 0 | 0 | 0 | 3,4 di-hydroxyphenyl | OH | H | OH | H |
| 54 | O | 1 | 3 | — | 0 | 0 | 0 | 0 | 3,4 di-hydroxyphenyl | OH | H | OH | H |
| 55 | O | 1 | 4 | — | 0 | 0 | 0 | 0 | 3,4 di-hydroxyphenyl | OH | H | OH | H |
| 56 | O | 1 | 5 | — | 0 | 0 | 0 | 0 | 3,4 di-hydroxyphenyl | OH | H | OH | H |
| 77 | O | 1 | 2 | O | 1 | 2 | 0 | 0 | 3,4 di-hydroxyphenyl | OH | H | OH | H |
| 94 | O | 1 | 2 | O | 1 | 2 | 1 | 0 | hydrogen | OH | H | OH | H |

V. CHARACTERIZATION AND PURIFICATION OF THE TARGETS

The synthetic chemistry outlined above can be carried out by standard methods apparent to those skilled in the art, and employ purification of reaction products by chromatography and/or crystallization. Product homogeneity can be ascer- 1–76 of the glucocorticoid receptor fused to amino acids 1–147 of the yeast transcription factor GAL4, including the DNA binding domain, in the pSG5 expression vector (Stratagene). cDNAs encoding amino acids 167–468, 138–440, and 174–475 of murine PPARα, NUC-1, and PPARγ1 are amplified by polymerase chain reaction and inserted C-terminal to GAL4 in the pSG5 expression vector (Stratagene) to generate plasmids pSG5-GAL4-PPARα, pSG5-GAL4-NUC-1, and pSG5-GAL4-PPARγ, respectively. The regions of the PPARs included in the chimeras should contain the ligand binding domains based on their homology to ligand binding domains of characterized nuclear receptors. The chimeras initially contained the translation start site and N-terminal 262 amino acids of the glucocorticoid receptor, including the $\tau_1$ transcriptional transactivation domain. However, as these chimeras had high basal activity in CV-1 cells, a 0.6-kilobase BglII fragment containing the $\tau_1$ domain can be removed, leaving the translation start site and amino acids 1–76 of the glucocorticoid receptor. Wild-type receptor expression vectors can be generated by insertion of cDNAs encoding murine PPARα, NUC-1, PPARγ1 and PPARγ2 into the expression vector pSG5 (Stratagene). Reporter plasmid (UAS)$_5$-tk-CAT can be generated by insertion of five copies of a GAL4 DNA binding element into the BamHI site of pBLCAT2. The reporter a P2-tk-CAT was generated by insertion of the 518-bp EcoRI/XBAI fragment containing the enhancer of the aP2 gene into the BamHI site of pBLCAT2.

Cotransfection Assay—CV-1 cells are plated in 24-well plates in DME medium supplemented with 10% delipidated fetal calf serum. In general, transfection mixes contain 10 ng of receptor expression vector, 100 ng of the reporter plasmid, 200 ng of β-galactosidase expression vector (pCH110, Pharmacia) as internal control, and 200 ng of carrier plasmid. Transfections can be done with Lipofectamine (Life Technologies, Inc.) according to the manufacturer's instructions. Cell extracts were prepared and assayed for chloramphenicol acetyltransferase and β-galactosidase activities as described previously.

Ligand Binding Assay—cDNA encoding amino acids 174–475 of PPARγ1 can be amplified via polymerase chain reaction and inserted into bacterial expression vector pGEX-2T (Pharmacia). GST-PPARγ LBD can be expressed in BL21(DE3)plysS cells and extracts prepared as described previously. For saturation binding analysis, bacterial extracts (100 μg of protein) is incubated at 4° C. for 3 h in buffer containing 10 mM Tris (pH 8.0), 50 mM KCl, 10 mM dithiothreitol with [$^3$H]-BRL49653 (specific activity, 40 Ci/mmol)in the presence or absence of unlabeled BRL49653. Bound can be separated from free radio-activity by elution through 1-ml Sephadex G-25 desalting columns (Boehringer Mannheim). Bound radioactivity eluted in the column void volume and can be quantiated by liquid scintillation counting.

VII. COMPOSITIONS AND METHODS

In another aspect, the present invention provides a pharmaceutical composition comprising a compound of the Formula I:

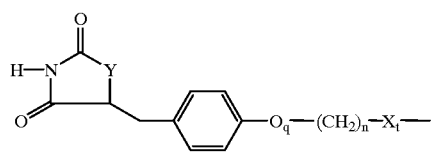

I

-continued

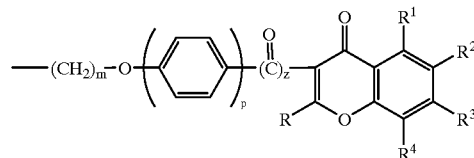

wherein Y, X, NR$^6$ R$^1$, R$^2$ R$^3$ and R$^4$, R, R$^{11}$, A, R$^{13}$, R$^{14}$, R$^{15}$, R$^{16}$, R$^{17}$, R$^{23}$, R$^{24}$, R$^{25}$, A, Q, x, y, h, s, k, r, s, T, Z, q, n, t, m, p and z have the same meaning as defined above, or a pharmaceutical acceptable salt or solvate thereof, and a pharmaceutical acceptable carrier.

The compounds of this invention can be formulated in a variety of carriers and delivery systems. For instance, to prepare a long-acting depot formulation, a therapeutically effective concentration of the compound is placed in an oil, resin, biopolymer or other suitable delivery device as is known in the art. The amount of the therapeutic compound to be administered and the compound's concentration in depot formulations depend upon the vehicle or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

In addition to the therapeutic compound, the compositions can include, depending on the formulation desired, pharmaceutically-acceptable non-toxic carriers, or diluents which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., Tris or phosphate buffers. Effective amounts of diluents, additives and excipients are those amounts which are effective to obtain a pharmaceutically acceptable formulation in terms of solubility, biological activity, etc.

Thus, a composition of the invention includes a therapeutic compound which can be formulated with conventional, pharmaceutically acceptable, vehicles for topical, oral or parenteral administration. Formulations can also include small amounts of adjuvants such as buffers and preservatives to maintain isotonicity, physiological and pH stability. Means of preparation, formulation and administration are known to those of skill. See generally Remington's Pharmaceutical Science 15th ed., Mack Publishing Co., Easton, Pa. (1980).

To prepare a topical formulation for the treatment of dermatological disorders listed in Tables II, III, IV & V, or diseases of the external eye (Table VII), a therapeutically effective concentration of the compound is placed in a dermatological vehicle as is known in the art. The amount of the therapeutic compound to be administered and the compound's concentration in the topical formulations depend upon the vehicle selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The concentration of the therapeutic compound for topical formulations is in the range of about 1 mg/mL to about 1000 mg/mL. Typically, the concentration of the therapeutic compound for topical formulations is in the range of about 2.5 mg/mL to about 25 mg/ml. Solid dispersions of the therapeutic compound as well as solubilized preparations can be used. Thus, the precise concentration is subject to modest experimental manipulation in order to optimize the therapeutic response. About 2,500 mg of therapeutic compound per 100 grams of vehicle is useful in the treatment of skin lesions to provide a 2.5% weight/weight (w/w) formulation. Suitable vehicles include oil-in-water or water-in-oil emulsions using mineral oils, petrolatum and the like as well as gels such as hydrogel.

Alternative topical formulations include shampoo preparations, oral paste, and mouth wash preparations. ORABASE7 can be used as the base oral paste to which the therapeutic compound is added. Concentrations of therapeutic compound are typically as stated above for topical formulations.

In yet another aspect, the present invention relates to a method of treating a PPARγ mediated disease, comprising administering a therapeutically effective amount of compound of the Formula I:

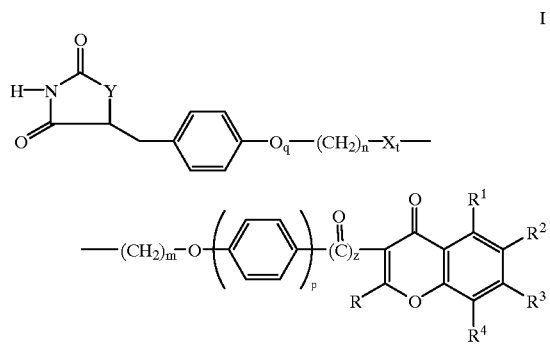

I wherein Y, X, $NR^6$, $R^1$, $R^2$, $R^3$ and $R^4$, R, $R^{11}$, A, $R^{13}$, $R^{14}$, $R^{15}$, $R^{16}$, $R^{17}$, $R^{23}$, $R^{24}$, $R^{25}$, A, Q, x, y, h, s, k, r, s, T, Z, q, n, t, m, p and z have the same meaning as defined above, to an individual suffering from a PPARγ mediated disease. Diseases treatable with the novel compounds described herein are outlined in Tables II, III, IV, V, VI & VII. These compounds have clinical utility in the treatment of non-malignant (Table II) and malignant (Table III) diseases in multiple organ systems, diseases caused by naked or coated DNA and RNA viruses, and local and disseminated diseases associated with the infection by these viruses (Table IV), human immunodeficiency virus (HIV) infection and diseases associated with HIV infection (Table V), neuropsychiatric diseases (Table VI), and diseases of the eye (Table VII).

The methods of treatment provided by this invention are practiced by administering to a human or vertebrate animal in need a dose of a compound of Formula I that binds to or modifies the activity of peroxisome proliferator activated receptor-gamma (PPARγ), or a pharmaceutically acceptable salt or solvate thereof. The present method includes both medical therapeutic and/or prophylactic treatment as necessary.

The compounds described in this invention can be use to treat a variety of disorders including proliferative, inflammatory, metabolic, or infectious disorders. The specific disorders that can be treated with the compounds described in this invention are listed in Tables II, III, IV, V, VI & VII.

Using methods of the invention, therapeutic compounds are typically administered to human patients topically or orally. Parenteral administration is used in appropriate circumstances apparent to the practitioner. Preferably, the compositions are administered in unit dosage forms suitable for single administration of precise dosage amounts. For example long-acting depot compositions are administered subcutaneously or intramuscularly as precise unit doses with each dose lasting weeks to months.

VIII. ADMINISTRATION

The therapeutic compound is optionally administered topically by the use of a transdermal therapeutic system (see, Barry, Dermatological Formulations, (1983) p. 181 and literature cited therein). While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane.

For ophthalmic applications (Table VII), the therapeutic compound is formulated into solutions, suspensions, and ointments appropriate for use in the eye. The concentrations are usually as discussed above for topico-local preparations. For ophthalmic formulations, see Mitra (ed.), *Ophthalmic Drug Delivery Systems*, Marcel Dekker, Inc., New York, N.Y. (1993) and also Havener, W. H., *Ocular Pharmacology*, C. V. Mosby Co., St. Louis (1983).

The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/mL. More typically, the concentration is from about 10 to 60 mg/mL or about 20 mg/mL. Concentrations below 1 mg/mL may be necessary in some cases depending on the solubility and potency of the compound selected for use. The formulation, which is sterile, is suitable for various parenteral routes including intra-dermal, intra-articular, intra-muscular, intravascular, and subcutaneous.

Slow or extended-release delivery systems, including any of a number of biopolymers (biological-based systems), systems employing liposomes, and polymeric delivery systems, can be utilized with the compositions described herein to provide a continuous or long term source of therapeutic compound. Such slow release systems are applicable to formulations for topical, ophthalmic, oral, and parenteral use.

IX. ROUTES OF ADMINISTRATION

Therapeutic agents of the invention are usually delivered or administered topically or by transdermal patches for treating disorders involving the skin that are listed in Tables II, III, IV, V, VI & VII. Oral administration is preferred for disorders in Tables II, III, IV, V, VI & VII that cannot be treated effectively by topical therapy. Additionally, the agents can be delivered parenterally for the conditions in listed in Tables II, III, IV, V, VI & VII, that do not respond to oral or topical therapy or for conditions where oral or topical therapy is not feasible. Parenteral therapy is typically intra-dermal, intra-articular, intramuscular or intravenous.

A preferred way to practice the invention for disorders in II, III, IV, V, & VII that affect the skin is to apply the compound of interest, in a cream, lotion, ointment, or oil based carrier, directly to the skin lesions. Typically, the concentration of therapeutic compound in a cream, lotion, or oil is 1–2%. Alternatively, an aerosol can be used topically. These compounds can also be orally administered.

In general, the preferred route of administration is oral, parenteral, or topical (including administration to the eye, scalp, and mucous membranes). Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia.

Oral administration is a preferred alternative for treatment of dermatological and eye diseases listed in Tables II, III, IV, V, VI & VII where direct topical application is not useful, and it is a preferred route for other non-dermatological applications. Intravenous administration may be necessary in disorders that cannot be effectively treated by topical or oral administration.

Intra-articular injection is a preferred alternative in cases of arthritis (psoriatic or nonpsoriatic) where the practitioner wishes to treat one or only a few (such as 2–6) joints. Usually, the compound is delivered in an aqueous solution of about 10–20 mg/ml. Additionally, the therapeutic compounds are injected directly into lesions (intra-lesion administration) in appropriate cases. Intradermal administration is an alternative for dermal lesions such as those of psoriasis.

For pulmonary applications, a chemical delivery system for drug targeting to lung tissue using a compound of Formula I as the "targetor moiety". Therefore a preferred therapeutic compound is compound 3 that modifies the activity of PPARγ and is formulated into solutions, suspensions, aerosols and particulate dispersions appropriate for application to the pulmonary system. The therapeutic agent may be inhaled via nebulizer, inhalation capsules, inhalation aerosol, nasal solution, intratracheal as a solution via syringe, or endotracheal tube as an aerosol or via as a nebulizer solution. In vitro kinetic and in vivo pharmacokinetics studies have shown that the compounds of Formula I provide an effective pulmonary delivery system which, in a sufficiently stable in buffer and biological media, is hydrolyzed rapidly into the respective active parent drugs, with significantly enhanced delivery and retention of the active compound to lung tissue.

X. DOSAGE AND SCHEDULES

An effective quantity of the compound of interest is employed in treatment. The dosage of compounds used in accordance with the invention varies depending on the compound and the condition being treated. The age, weight, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 100 to about 600 mg twice a day. More typically, a single dose is about 100–200 mg of compound given twice a day. A convenient oral dose for an adult patient is 200 mg twice a day. A dosage range for topical treatment is about 0.1% to about 10% (weight/volume) in a cream or ointment, applied twice a day. A usual dose for intra-articular injection is 20–40 mg injected per joint, not generally exceeding three joints per therapy session. A typical dosage for intra-dermal administration is about 20–75 mg per injection per site. A typical dosage for intravenous or intramuscular administration in an adult patient would be between 1 mg and 1000 mg per day given in single or divided doses depending on the judgement of the practitioner.

In some aspects, for example a thiazolidinedione, the oral dose is determined from the following formula:

$$\text{Oral dose (in milligrams)} = (k_1)(EC_{50})(k_2)(LBW)(MW);$$

wherein $k_1$ is a dimensionless constant with values ranging from 5 to 100; $EC_{50}$ is in mol/L;

$k_2$ is the fractional water content of the lean body weight (LBW) of the patient=0.72 L/kg, (see, *GEIGY SCIENTIFIC TABLES*, VOL 1, Lentner (ed.), p217, Ciba-Geigy Limited, Basle, Switzerland (1981); and MW is the molecular weight of the drug in g/mol.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued.

Occasionally, side effects warrant discontinuation of therapy. In general, an effective amount of the compound is that which provides either subjective relief of symptoms or an objectively identifiable improvement as noted by the clinician or other qualified observer.

The compounds in this invention can also be given orally in combination with compounds that bind or modify the activity of the vitamin D receptor or in combination with compounds that bind or modify the activity of the retinoid X receptors or retinoic acid receptors to provide for a synergistic effect in the treatment or prevention of the disorders listed in Tables II, III, IV, V, VI & VII. Examples of such compounds that provide for synergistic effect when given in combination with the drugs encompassed by the current invention include vitamin D analogs, various retinoic acid derivatives, and other ligands for retinoid X receptors or retinoic acid receptors including but not limited to compounds such as LG100268, tazarotene, TTNPB, or LGD1069 (Targretin).

Synergistic therapeutic effects can be achieved by oral administration of the drugs encompassed in the current invention together with orally or intravenously administered drugs that bind to and or modify the activity of either the vitamin D receptor or retinoid X receptors or retinoic acid receptors. As such, in another embodiment, the present invention relates to a method of treating a PPARγ mediated disease, comprising administering a combination therapy of a compound of Formula I and a member selected from the group consisting of a drug that bind to or modifies the activity of a vitamin D receptor, a retinoid X receptor, or a retinoic acid receptor.

A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without compounds of Formula I. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D (1,25-(OH)$_2$-vit D) and calcipotriene. The dosage range and routes and frequency of administration of compounds of Formula I required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. Synergistic therapeutic effects can also be achieved for conditions that are treated by topical administration of vitamin D derivatives or retinoid related compounds such as psoriasis, acne, or other disorders not involving the skin described in Tables II, III, IV, V, VI & VII. The dosages and the modes and frequency of administration of the vitamin D or retinoid related compounds for synergistic topical therapy would be similar to those ordinarily recommended for these agents when given without compounds of Formula I. The dosage range and the modes and frequency required for topical administration of the compounds of Formula I given in combination with vitamin D or retinoid related compounds are the same as those described elsewhere in this disclosure.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, the invention has been described with human patients as the usual recipient, but veterinary use is also contemplated.

XI. EXAMPLES

General. All reactions were carried out under an argon atmosphere with dry, freshly distilled solvents under anhydrous conditions, unless otherwise stated. Acetone was distilled from potassium carbonate, and N, N-dimethylformamide (DMF), from calcium hydride. Yields were applied to chromatographically and spectroscopically ($^1$H-NMR) homogeneous materials. Reagents were purchased at highest commercial quality and used without further purification unless otherwise mentioned. Reactions were monitored by thin-layer chromatography carried out on 250 microns Analtech, Inc. silica gel plates, employing UV light and p-anisaldehyde solution and heat to visualize the distributions of compounds. Silica gel (60 Å, 230–400 mesh) (Whatman Inc.) was used for flash column chromatography. Preparative thin-layer chromatography (PTLC) separations were carried out on 1000 microns silica gel plates (Analtech). NMR spectra were obtained by Bruker Advance DXR-400 or DXR-300 instruments and calibrated using tetramethylsilane. Abbreviations were used to explain multiplicities as followings: s=singlet, d=doublet, t=triplet, q=quartet, qui=quintet, m=multiplet, b=broad.

EXAMPLE 1

This example illustrates the synthesis of compound 3.

4-(3-bromopropyloxy)benzaldehyde (37) (see, FIG. 8A). K$_2$CO$_3$ (1.82 g, 13 mmol) and 1,3-dibromopropane (3.05 mL, 30 mmol) were added to a solution of 4-hydroxybenzaldehyde (1.22 g, 10 mmol) in acetone (30 mL). The mixture was heated under reflux for 8.5 hrs. Then the reaction mixture was filtered and the solvent was removed by evaporation. The resulting residue was mixed with ether and then washed consecutively with 5% NaOH, water, and brine. After drying with MgSO$_4$ and evaporation of the solvent, flash column chromatography (silica gel, hexane 100%>EtOAc:hexane=10:90>20:80) gave the desired compound as a pale yellow oil: Rf=0.71 (silica gel, EtOAc:hexane=35:65); yield 61%; $^1$H-NMR (300 MHz, CDCl$_3$) δ9.86 (1H, s), 7.82–7.79 (2H, dd, J=6.9 and 1.8 Hz), 7.00–6.97 (2H, dd, J=7.1 and 1.6 Hz), 4.19–4.15 (2H, t, J=5.8 Hz), 3.61–3.56 (2H, t, 6.4 Hz), 2.37–2.28 (2H, qui, 6 Hz).

5,7,3',4'-Tetra-O-benzylquercitin (26) (see, FIG. 7B). K$_2$CO$_3$ (2.26 g, 16 mmol) and benzylbromide (1.95 mL, 16 mmol) were added to a solution of rutin (1.0 g, 1.6 mmol) in DMF (10 mL). The mixture was heated at 110° C. for 11 hrs. Then the reaction mixture was filtered, and water and EtOAc were added for extraction. 5% NaOH, water and brine were used to wash the combined EtOAc layer. The EtOAc layer was dried with MgSO$_4$ and the solvent was removed by evaporation. Flash column chromatography (silica gel, EtOAc:MeOH=98:2>95:5) provided solid compound 16 (R is benzyl): Rf=0.55 (silica gel, EtOAc:MeOH=95:5). Hydrolysis of 16 (1.17 g, 1.2 mmol) was carried out with CHCl₃ (37%, 20 mL), stirring at r.t. for 2 hrs. The reaction mixture was quenched with water and extracted with EtOAc. The combined EtOAc layer was washed with water and brine, dried with $MgSO_4$ and removed by evaporation. Flash column chromatography (silica gel, EtOAc hexane=15:85→20:80) gave compound 26 as a yellow solid: Rf=0.3 (silica gel, EtOAc:hexane=20:80, 1% AcOH); yield 21%; ¹H-NMR (400 MHz, CDCl₃) δ11.70 (1H, s), 7.92 (1H, s), 7.75 (1H, d, J=7.2 Hz), 7.62–7.20 (20H, m), 7.00 (1H, d, J=7.1 Hz), 6.54 (1H, s), 6.44 (1H, s), 5.25 (2H, s), 5.22 (2H, s), 5.19 (2H, s), 5.10 (2H, s).

NaH (20 mg, 0.46 mmol) and 37 (92.35 mg, 0.38 mmol) were added to a solution of 26 (250 mg, 0.38 mmol) in DMF (7 mL). The reaction mixture was stirred at r.t. for 2 hrs. Then the reaction mixture was quenched with ice and extracted with EtOAc. The combined EtOAc layer was washed with water and brine, dried with $MgSO_4$, and removed by evaporation. Flash column chromatography (silica gel, EtOAc:hexane=30:70→40:60) gave the intermediate 3-carbon tether aldehyde compound (see, FIG. 7B, similar to compound 34 however with a 3 carbon tether) as a light yellow solid: $R_f$=0.24 (silica gel, EtOAc:hexane=20:80); yield 67%; ¹H-NMR (400 MHz, CDCl₃) δ9.79 (1H, s), 7.75–7.73 (2H, d, J=8 Hz), 7.66 (1H, d, J=2 Hz), 7.59–7.57 (2H, d, J=8 Hz), 7.46–7.28 (20 Hz, m), 6.88 (1H, d, J=3 Hz), 6.86 (1H, d, J=3 Hz), 6.52 (1H, d, J=2 Hz), 6.44 (1H, d, J=2 Hz), 5.25 (2H, s), 5.18 (2H, s), 5.14 (2H, s), 5.08 (2H, s), 4.19 (2H, t), 4.08 (2H, t), 2.22–2.10 (2H, m).

2,4-thiazolidinedione (56 mg, 0.48 mmol) and piperidine (4.8 μL, 0.048 mmol) were added to a solution of intermediate 3-carbon tether aldehyde compound from the previous step (100 mg, 0.12 mmol) in EtOH (2 mL). The reaction mixture was heated at 100° C. for 10 hrs in a pressure-resistant container. Since the intermediate 3-carbon tether aldehyde compound was a solid precipitation, it was filtered and washed with EtOH. It was then applied to vacuum pump to dry completely: Rf=0.51 (EtOAc:hexane=50:50); yield 36%; ¹H-NMR (300 MHz, DMSO) δ12.4 (1H, s), 7.70–7.68 (2H, d, J=6.6 Hz), 7.63–7.61 (2H, d, J=7.7 Hz), 7.51–7.31 (21H, m), 7.00–6.88 (4H, m), 6.70 (1H, s), 5.23 (4H, s), 5.17 (2H, s), 5.04 (2H, s), 4.12–4.09 (2H, t, J=5.6 Hz) 4.09–4.05 (2H, t, J=6.0 Hz), 2.05 (2H, m).

Compound 3 is then generated with catalytic hydrogenation over Pd/C.

EXAMPLE 2

This example illustrates a clinical trial and therapy by topical application.

A patient having dermal manifestations of either psoriasis vulgaris, or acne vulgaris, or human papilloma virus (HPV) infection (e.g., anogenital warts) is selected for therapy using the invention. A compound of Formula I that modifies the activity of PPARγ is prepared in a cream vehicle at a concentration of 1 to 5% (weight/volume), typically 2.5% and is applied to the affected skin three times a day. After the skin lesions have subsided, therapy is discontinued.

EXAMPLE 3

This example illustrates a clinical trial and therapy by oral administration.

A patient having type 2 diabetes mellitus, or chronic generalized acne, or chronic generalized psoriasis, with or without psoriatic arthritis, or rheumatoid arthritis, or inflammatory bowel disease (e.g., ulcerative colitis) is selected for therapy. The patient weighs 80 kilograms. For infants or children the doses suggested are lowered in a linear fashion based on body weight or surface area. The female patient of child-bearing potential is given a pregnancy test to confirm that the patient is not pregnant. Provided that the patient is not pregnant and does not plan to become pregnant during treatment, a compound of Formula I that modifies the activity of PPARγ is orally administered in a dosage of 20 to 1,000 milligrams twice daily, more typically 100 mg twice daily. The patient is monitored for improvement in the manifestations of the index disease. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered when the manifestations of the disease subside, or discontinued if indicated.

EXAMPLE 4

This example illustrates a clinical trial and therapy by intravenous injection administration.

A patient having non-metastatic cancer, such as breast cancer, prostate cancer or colon cancer is selected for therapy. The patient weighs 80 kilograms. For infants or children the doses suggested are lowered in a linear fashion based on body weight or surface area. The female patient of child-bearing potential is given a pregnancy test to confirm that the patient is not pregnant. If indicated, the tumor is surgically excised. When the patient is stable post-surgically, a compound of Formula I that modifies the activity of PPARγ administered intravenously in a dose of 50 to 1,000 mg, more typically in a dosage of 200 milligrams, as a bolus or continuous infusion over 4 hr, every 12 hr. The patient is monitored for improvement in his or her manifestations of the cancer in terms of laboratory tests such as prostate specific antigen (PSA) for prostatic cancer, or carcinoembryonic antigen (CEA) for breast or colon cancer. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered when the manifestations of the disease subside, or discontinued if indicated.

EXAMPLE 5

This example illustrates a clinical trial and therapy by intralesional injection administration.

The patient is one who has venereal warts (HPV infection), or dermatological manifestations of Kaposi sarcoma (with or without infection with the human immunodeficiency virus) who is not a candidate for surgery, or in whom surgery may impair bodily functions (such as painful sexual activity, or impairment in urination or defecation in the case of venereal warts). The patient is treated by administering, intralesionally, injection(s) of a compound of Formula I that modifies the activity of PPARγ. The compound is administered in a 5 to 50 mg/mL, more typically 20 mg/mL of an aqueous solution, a suspension or an emulsion. About 10–75 mg are injected directly into each lesion, depending on its size and volume. The therapy is repeated weekly until the lesions are eradicated.

EXAMPLE 6

This example illustrates a clinical trial and therapy by intra-articular injection administration.

A patient having psoriatic arthritis or rheumatoid arthritis with painful, swollen, inflamed joints, is treated with intra-articular injection(s) of a compound of Formula I that modifies the activity of PPARγ. The compound is administered in a 5 to 50 mg/mL, more typically 20 mg/mL of an aqueous solution, a suspension or an emulsion. About 10–50 mg are injected directly into each joint, depending on the joint and the severity of the disease. The therapy is repeated weekly until the disease subsides and the pain and inflammation resolves.

EXAMPLE 7

This example illustrates a clinical trial and therapy by intrathecal injection administration.

A patient having viral meningitis (e.g., meningitis caused by cytomegalovirus), is treated with intrathecal injection(s) of a compound of Formula I that modifies the activity of PPARγ. The compound is administered by injection or via catheter, in a 5 to 50 mg/mL (more typically 20 mg/mL) of an aqueous solution, a suspension or an emulsion. About 10–50 mg, depending on the patient's lean body-mass and the severity of the disease, is injected directly into the intrathecal space. The therapy is administered 3 time a week and tapered to once weekly as symptoms subside, and eventually discontinued when the infectious agent is eradicated.

EXAMPLE 8

This example illustrates a clinical trial for ocular therapy by topical application.

For ophthalmic applications, the therapeutic compound is a compound of Formula I that modifies the activity of PPARγ and is formulated into solutions, suspensions, and ointments appropriate for application to the external eye. The formulation contains the drug at a concentration of 20 mg/mL. A patient having allergic conjunctivitis, or viral conjunctivitis, or keratitis, or uveitis is treated by topico-local administration of the optic formulation, with 2 to 3 drops being instilled in each eye and the process repeated every 4 hr for 2 wk or more, depending on the type or severity of the disease, until the symptoms have subsided or resolved.

EXAMPLE 9

This example illustrates a clinical trial for pulmonary therapy.

The preferred therapeutic compound is 3 which modifies the activity of PPARγ and is formulated into solutions, suspensions, aerosols and particulate dispersions appropriate for application to the pulmonary system. The patient weighs 80 kilogram. For infants or children the doses suggested are lowered in a linear fashion based on body weight or surface area. The patient has asthma or COPD. The therapeutic agent may be inhaled via nebulizer, inhalation capsules, inhalation aerosol, nasal solution, intratracheal as a solution via syringe, or endotracheal tube as an aerosol or via as a nebulizer solution. For delivery via nebulizer, the therapeutic agent is given at a dose of 0.5 to 50 mg per 2 mL solution, more typically 10 mg/2 mL dose given every 15 min as needed for acute treatment. For delivery by metered dose inhaler, the therapeutic agent is given at a dose of 0.05 to 1.0 mg per actuation, more typically 0.2 mg per actuation, given every 4 hr.

TABLE II

Examples of non-malignant proliferative, inflammatory disorders treatable with compounds described in this invention

| Organ System | Disease/Pathology |
| --- | --- |
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratoses, senile keratosis, actinic keratosis, photo-induced keratosis, skin ageing, including photo-induced skin aging, keratosis follicularis; keloids and prophylaxis against keloid formation; leukoplakia, lichen planus, keratitis, contact dermatitis, eczenia, urticaria, pruritus, hidradenitis, acne inversa. |
| Cardiovascular | Hypertension, vasculo-occlusive diseases including atherosclerosis, thrombosis and restenosis after angioplasty; acute coronary syndromes such as unstable angina, myocardial infarction, ischemic and non-ischeinic cardiomyopathies, post-MI cardiomyopathy and myocardial fibrosis, substance-induced cardiomyopathy. |
| Endocrine | Insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, polycystic kidney disease, diabetic nephropathy. |
| Pulmonary | Asthma, chronic obstructive pulmonary disease (COPD), reactive airway disease, pulmonary fibrosis, pulmonary hypertension. |
| Immunological/ Connective tissue/ Joints | Rheumatoid arthritis, Raynaud's phenomenon/disease, Sjogren's syndrome systemic sclerosis, systemic lupus erythematosus, vasculitides, ankyiosing spondylitis, osteoarthritis, reactive arthritis, psoriatic arthritis, fibromyalgia. |
| Other | Fibrocystic breast disease, fibroadenoma, chronic fatigue syndrome. |

TABLE III

Examples of neoplastic diseases or malignancies diseases treatable with compounds described in this invention

| Organ System | Malignancy/Cancer type |
|---|---|
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone receptor. positive or negative subtypes, soft tissue tumors. |
| Metastasis | Metastases resulting from the neoplasms. |
| Other | Angiomata, angiogenesis associated with the neoplasms. |

TABLE IV

Examples of viral infections and related pathologies treatable with compounds described in this invention

| Virus | Viral infection/cancer or other virus-associated pathology |
|---|---|
| HTLV | T-cell leukemia/lymphoma, HTLV-associated arthritides/myelopathies. |
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, variceila-zoster, chicken pox, herpes zoster, post-herpetic neuralgia, conjunctivitis, keratoconjunctivitis, keratitis. |
| HHV | Exanthem subitum, infectious mononucleosis. |
| EBV | Infectious mononucleosis, chronic fatigue syndrome, lymphoma, conjunctivitis, keratitis, and related infections of the eye. |
| Adenoviruses | Upper and lower respiratory tract infections, pneumonia, conjunctivitis. |
| RSV | Upper and lower respiratory tract infections, pneumonla. |
| PMV | Mumps and related manifestations, e.g., conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumonia. |

HIV, Human Immunodeficiency Virus; HTLV, Human T-cell Lymphocyte Virus; HPV, Human Papilloma Virus; HAV, Hepatitis A Virus; HBV, Hepatitis B Virus; HAV, Hepatitis C Virus; CMV, Cytomegalovirus; HSV, Herpes Simplex Virus (Types I & II); HHV, Human Herpes Virus; EBV, Epstein-Barr Virus; RSV, Respiratory Syncytial Virus; VZV, Varicella-Zoster Virus; PMV, Paramyxovirus; MV, Measles (Rubeola) Virus; RV, Rubella Virus

TABLE V

HIV related infections and diseases treatable with compounds described in this invention

| Organ system | Viral infection/manifestation or other HIV-associated disease |
|---|---|
| Immunologic | AIDS, primary HIV infection. |
| Dermatological | Anogenital cancers including rectal and cervical cancer, Kaposi's sarcoma, squamous cell carcinoma, hairy leukoplakia, molluscum contagiosum, warts (HPV infections), seborrheic dermatitis, psoriasis, xeroderma, HSV and varicella-zoster infections. |
| Hematologic | Non-Hodgkin's lymphoma, B cell lymphoma, anemia, neutropenia, thrombocytopenia. |
| Gastrointestinal | Anorexia, gastroparesis, diarrhea, malabsorption, gastrointestinal CMV infections, esophagitis, colitis, hepatitis, lymphoma. |
| Ocular | Conjunctivitis, keratitis, keratoconjunctivitis, uveitis, retinitis, chorioretinitis, CMV retinitis, iridocycliti s, vitreitis, choroiditis, papilledema, Kaposi's sarcoma, lymphoma, ocular palsies, conjunctival warts, pre-neoplastic and neoplastic diseases of the eye. |
| CardiacMyocarditis, | endocarditis, pericarditis. |
| Pulmonary | CMV pneumonitis, lymphoid interstitial pneumonitis. |
| Nephroiogic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome, chronic pain, psychoses, substanee abuse disorders and drug addiction. |
| GeneralLymphoma, | metastatic lymphoma, Kaposi's sarcoma, wasting syndrome. |

TABLE VI

Examples of neurological and psychiatric disorders that can be treated with compounds described in this invention Neurological Disorders Migraine headaches
Alzheimer's disease
Parkinson's disease
Pain disorders including algesia, hyperalgesia, acute and
chronic pain, allodynia
Chronic fatigue syndrome
Amnesia Psychiatric Disorders Dysphoric mood disorders
Dysthymic disorder
Depression including depression associated with chronic
diseases and medications
Manic depressive disorder
Anxiety states including panic disorder and agoraphobia
Post menstrual syndrome
Obsessive-compulsive disorder, schizophrenia, chronic fatigue syndrome
Substance abuse and drug addiction

TABLE VII

Diseases of the eye treatable with compounds described in this invention

1. Diseases caused by viruses or associated with viral infections Disease Virus

| | |
|---|---|
| Blepharitis | HSV, VZV, Vaccinia, HPV, molluscum contagiosum |
| Conjunctivitis | HSV, VZV, EBV, adenovirus, vaccinia, variola, HPV, molluscum contagiosum, influenza |
| Follicular c. | Newcastle, measles, mumps, rubella, molluscum contagiosum |
| Hemorrhagic c. | Enterovirus, coxsackie |
| Catarrhal c | Rubella |
| Keratitis | HSV; VZV, EBV, Adenovirus, Vaccinia, Variola, HPV, molluscum contagiosum |
| Keratoconjunctivitis | HSV, VZV, EBV, Adenovirus, Vaccinia, Variola, HPV, molluscum contagiosum |
| Retinitis | CMV |
| Uveitis | HPV |
| Conjunctival warts | HPV |
| C. epithelial neoplasms | HPV |

2. Ocularplastic diseases

Benign tumors: Keratocanthoma, molluscum contagiosum, dermoid cysts, neurofibroma, neurofibromatosis, schwannoma (neurilemoma), pleiomorphic adenoma
Malignant tumors: Basal cell carcinoma, squamous cell carcinoma, mucoepidermoid carcinoma, melanorna, retinoblastoma, embryonal rhabdomyosarcoma, meningioma, adenoid cystic carcinoma, lymphoid tumors of the orbit, mesenchymal tumors (fibrous hystiocytoma) of the orbit, nasopharyngeal carcinoma.
Vascular lesions: Hemangioma, lymphangioma.

3. Inflammatory/immunological ocular diseases

Acute allergic conjunctivitis and hypersensitivity reactions
Drug-related inflammation and hypersensitivity reactions
Chronic (vernal) conjunctivitis
Contact lens-associated conjunctivitis, e.g. giant papillary conjunctivitis
Cojunctival ulceration, including ulceration associated with mucous membrane pemphigoid and the Steven's-Johnson syndrome, leading to progressive fibrosis and scarring, cicatrization and symblepharon.

4. Other lesions

Retina: Macular degeneration, retinopathy, including diabetic r. and hypertensive r.
Lens: Cataract, all etiologies includiiig rheumatological and collagen vascular diseases
Uvea: Ueitis, vitreitis, all etiologies, including UV radiation and diabetes.

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of the formula

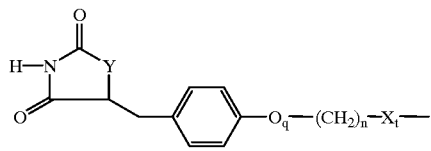

I

-continued

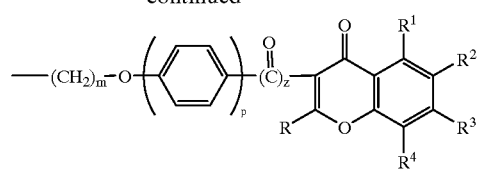

wherein:
Y is S;
X is a member selected from the group consisting of O, S and $NR^6$, wherein $R^6$ is a member selected from the group consisting hydrogen and optionally substituted $(C_1-C_{10})$alkyl;
$R^1$, $R^2$, $R^3$ and $R^4$ are members independently selected from the group consisting of hydrogen, hydroxy, halogen, optionally substituted $(C_1-C_6)$alkyl, optionally substituted $(C_1-C_{20})$alkoxy, $(C_1-C_6)$alkylcarbonyl, $(C_1-C_{20})$alkenyl, $R^{24}R^{23}N(CH_2)_xCH(OH)(CH_2)_yO-$, optionally substituted aroyl and aryl $(C_1-C_{10})$alkylcarbonyl;
R is a member selected from the group consisting of hydrogen, phenyl, 3,4-dihydroxyphenyl and $R^{11}$, wherein
$R^{11}$ is a member selected from the group consisting of $-A-NR^{13}R^{14}$, $-CONHR^{15}$, $-A-S-R^{16}$ and $-COOR^{17}$, wherein A denotes a lower alkylene group;

$R^{13}$ and $R^{14}$ are members independently selected from the group consisting of hydrogen, ($C_1$–$C_6$)alkyl, cycloalkyl and a sulfur- and a nitrogen-containing 5- or 6-membered heterocyclic ring, wherein said heterocyclic ring may be optionally substituted by one or two hydroxyl groups, or, alternatively, $R^{13}$ and $R^{14}$ together with the nitrogen to which they are bound form a pyrrolidine, piperidine or morpholine ring;

$R^{15}$ is a member selected from the group consisting of hydrogen and optionally substituted ($C_1$–$C_6$)alkyl;

$R^{16}$ is a member selected from the group consisting of ($C_1$–$C_6$)alkyl and a sulfur- and nitrogen containing 5- or 6-membered heterocyclic ring wherein said heterocyclic ring may be optionally substituted by one or two hydroxyl groups, carboxyl groups, or ($C_1$–$C_6$) alkoxycarbonyl groups;

$R^{17}$ is optionally substituted ($C_1$–$C_6$)alkyl;

$R^{23}$ is a member selected from the group consisting of hydrogen and optionally substituted ($C_1$–$C_6$)alkyl;

$R^{24}$ is a member selected from the group consisting of phenyl, benzyl, and $R^{25}(CH_2)_sCH(T)(CH_2)_k$, or a heterocyclic ring having the formula

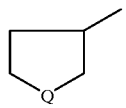

or alternatively, together with $R^{23}$ and the nitrogen atom to which they are bound form a 5- or 6-membered heterocyclic ring having the formula

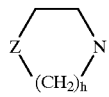

$R^{25}$ is either phenoxy or unsubstituted, monosubstituted, or disubstituted Ar, wherein, Ar is a member selected from the group consisting of phenyl, pyridinyl, furanyl, thiophenyl, naphthyl, each substituent of monosubstituted Ar is a member selected from the group consisting of hydroxy, ($C_1$–$C_6$)alkoxy, and $O(CH_2)_r CO_2R^{23}$, each substituent of disubstituted Ar is independently hydroxy or ($C_1$–$C_6$)alkoxy, Q is a member selected from the group consisting of $SO_2$, S, or O;

x is an integer from 1 to 5;

y is an integer from 1 to 5;

h is an integer from 1 to 2;

k is an integer from 1 to 7;

r is an integer from 0 to 2;

s is a integer from 0 to 6;

T is either hydrogen or OH;

Z is a member of the group consisting of $CH_2$, O, NH, $NCH_3$, and

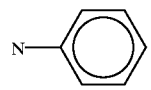

q is an integer from 0 to 1;

n is an integer from 0 to 5;

t is an integer from 0 to 1;

m is an integer from 0 to 2;

p is an integer from 0 to 1;

z is an integer from 0 to 1; provided that (1) at least one of x and y is one and (2) s plus k total no more than 7.

2. A compound in accordance with claim 1, wherein:

Y is S;

X is a member selected from the group consisting of O, S and $NR^6$, wherein $R^6$ a member selected from the group consisting hydrogen and optionally substituted ($C_1$–$C_6$)alkyl;

R is a member selected from the group consisting of hydrogen and 3,4-dihydroxyphenyl;

$R^1$ and $R^3$ are each hydroxy;

$R^2$ and $R^4$ are each hydrogen;

q is an integer from 0 to 1;

n is an integer from 0 to 5;

t is an integer from 0 to 1;

m is an integer from 0 to 2:

p is an integer from 0 to 1; and z is 0.

3. A compound in accordance with claim 2, wherein

Y is S;

R is 3,4-dihydroxyphenyl;

q is 1;

n is 1 to 5;

t is 0;

m is 0; and p is 0.

4. A compound in accordance with claim 3, wherein n is 1.

5. A compound in accordance with claim 3, wherein n is 2.

6. A compound in accordance with claim 3, wherein n is 3.

7. A compound in accordance with claim 3, wherein n is 4.

8. A compound in accordance with claim 3, wherein n is 5.

9. A compound in accordance with claim 2, wherein

Y is S;

R is 3,4-dihydroxyphenyl;

q is 0;

n 1 to 5;

t is 0;

m is 0; and p is 0.

10. A compound in accordance with claim 9, wherein n is 2.

11. A compound in accordance with claim 9, wherein n is 3.

12. A compound in accordance with claim 2, wherein

R is 3,4-dihydroxyphenyl;
q is 1;
n is 2
t is 1;
m is 2; and
p is 0.

13. A compound in accordance with claim 12, wherein
Y is S; and
X is 0.

14. A compound in accordance with claim 12, wherein
Y is S; and
X is $NR^6$, wherein $R^6$ is ethyl.

15. A compound in accordance with claim 2, wherein
R is H;
q is 1;
t is 0;
n is 1 to 5;
m is 0; and
p is 1.

16. A compound in accordance with claim 15, wherein
n is 1.

17. A compound in accordance with claim 15, wherein
n is 2.

18. A compound in accordance with claim 15, wherein
n is 3.

19. A compound in accordance with claim 15, wherein
n is 4.

20. A compound in accordance with claim 15, wherein
n is 5.

21. A compound in accordance with claim 2, wherein
R is H;
q is 1;
t is 1;
n is 2;
m is 2; and
p is 1.

22. A pharmaceutical composition comprising a compound of the compound of the formula

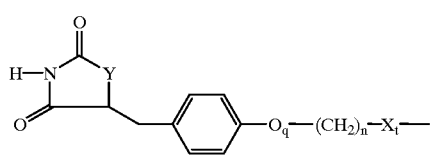
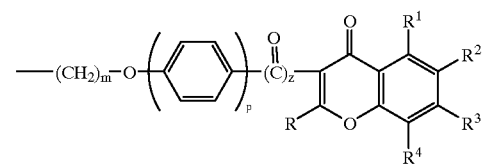

I wherein:
Y is S;
X is a member selected from the group consisting of O, S and $NR^6$, wherein $R^6$ is a member selected from the group consisting hydrogen and optionally substituted $(C_1-C_{10})$alkyl;
$R^1$, $R^2$, $R^3$ and $R^4$ are members independently selected from the group consisting of hydrogen, hydroxy, halogen, optionally substituted $(C_1-C_6)$alkyl, optionally substituted $(C_1-C_{20})$alkoxy, $(C_1-C_6)$alkylcarbonyl, $(C_1-C_{20})$alkenyl, $R^{24}R^{23}N(CH_2)_xCH(OH)(CH_2)_yO$—, optionally substituted aroyl and aryl $(C_1-C_{10})$alkylcarbonyl;

R is a member selected from the group consisting of hydrogen, phenyl, 3,4-dihydroxyphenyl and $R^{11}$, wherein $R^{11}$ is a member selected from the group consisting of —A—$NR^{13}R^{14}$, —$CONHR^{15}$, —A—S—$R^{16}$ and —$COOR^7$, wherein A denotes a lower alkylene group;

$R^{13}$ and $R^{14}$ are members independently selected from the group consisting of hydrogen, $(C_1-C_6)$alkyl, cycloalkyl and a sulfur- and a nitrogen-containing 5- or 6-membered heterocyclic ring, wherein said heterocyclic ring may be optionally substituted by one or two hydroxyl groups, or, alternatively, $R^{13}$ and $R^{14}$ together with the nitrogen to which they are bound form a pyrrolidine, piperidine or morpholine ring;

$R^{15}$ is a member selected from the group consisting of hydrogen and optionally substituted $(C_1-C_6)$alkyl;

$R^{16}$ is a member selected from the group consisting of $(C_1-C_6)$alkyl and a sulfur- and nitrogen containing 5- or 6-membered heterocyclic ring wherein said heterocyclic ring may be optionally substituted by one or two hydroxyl groups, carboxyl groups, or $(C_1-C_6)$alkoxycarbonyl groups;

$R^{17}$ is optionally substituted $(C_1-C_6)$alkyl;

$R^{23}$ is a member selected from the group consisting of hydrogen and optionally substituted $(C_1-C_6)$alkyl;

$R^{24}$ is a member selected from the group consisting of phenyl, benzyl, and $R^{25}(CH_2)_sCH(T)(CH_2)_k$, or a heterocyclic ring having the formula $$\begin{array}{c} \text{[ring structure with Q]} \end{array}$$

or alternatively, together with $R^{23}$ and the nitrogen atom to which they are bound form a 5- or 6-membered heterocyclic ring having the formula $$\begin{array}{c} \text{[ring structure with Z, N, (CH}_2\text{)}_h\text{]} \end{array}$$

$R^{25}$ is either phenoxy or unsubstituted, monosubstituted, or disubstituted Ar, wherein, Ar is a member selected from the group consisting of phenyl, pyridinyl, furanyl, thiophenyl, naphthyl, each substituent of monosubstituted Ar is a member selected from the group consisting of hydroxy, $(C_1-C_6)$alkoxy, and $O(CH_2)_rCO_2R^{23}$, each substituent of disubstituted Ar is independently hydroxy or $(C_1-C_6)$alkoxy, Q is a member selected from the group consisting of $SO_2$, S, or O;

x is an integer from 1 to 5;
y is an integer from 1 to 5;
h is an integer from 1 to 2;
k is an integer from 1 to 7;

r is an integer from 1 to 2;

s is a integer from 0 to 6;

T is either hydrogen or OH;

Z is a member of the group consisting of $CH_2$, O, NH, $NCH_3$, and

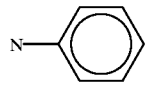

q is an integer from 0 to 1;

n is an integer from 0 to 5;

t is an integer from 0 to 1;

m is an integer from 0 to 2;

p is an integer from 0 to 1;

z is an integer from 0 to 1; provided that (1) at least one of x and y is one and (2) s plus k total no more than or a pharmaceutical acceptable salt or solvate thereof; and a pharmaceutical acceptable carrier.

23. A composition in accordance with claim 22, wherein:

Y is S;

X is a member selected from the group consisting of O, S and $NR^6$, wherein $R^6$ a member selected from the group consisting hydrogen and optionally substituted $(C_1-C_6)$alkyl;

R is a member selected from the group consisting of H and 3,4-dihydroxyphenyl;

$R^1$ and $R^3$ are each hydroxy;

$R^2$ and $R^4$ are each hydrogen;

q is an integer from 0 to 1;

n is an integer from 0 to 5;

t is an integer from 0 to 1;

m is an integer from 0 to 2;

p is an integer from 0 to 1; and z is 0.

24. A composition in accordance with claim 23, wherein

Y is S;

R is 3,4-dihydroxyphenyl;

q is 1;

n is 1 to 5;

t is 0;

m is 0; and p is 0.

25. A composition in accordance with claim 23, wherein

Y is S;

R is 3,4-dihydroxyphenyl;

q is 0;

n is 1 to 5;

t is 0;

m is 0; and p is 0.

26. A method of treating a PPARγ mediated disease, said method comprising administering a therapeutically effective amount of a compound of the formula

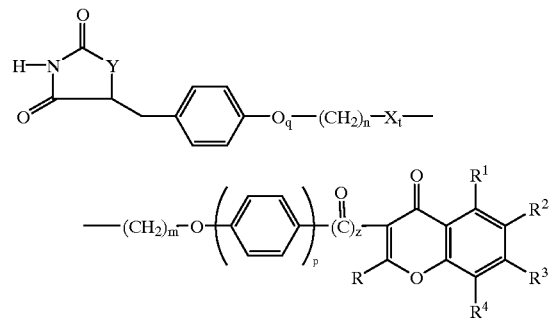

wherein:

Y is S;

X is a member selected from the group consisting of O, S and $NR^6$, wherein $R^6$ is a member selected from the group consisting hydrogen and optionally substituted $(C_1-C_{10})$alkyl;

$R^1$, $R^2$, $R^3$ and $R^4$ are members independently selected from the group consisting of hydrogen, hydroxy, halogen, optionally substituted $(C_1-C_6)$alkyl, optionally substituted $(C_1-C_{20})$alkoxy, $(C_1-C_6)$ alkylcarbonyl, $(C_1-C_{20})$alkenyl, $R^{24}R^{23}N(CH_2)_xCH(OH)(CH_2)_yO$—, optionally substituted aroyl and aryl $(C_1-C_{10})$alkylcarbonyl;

R is a member selected from the group consisting of hydrogen, phenyl, 3,4-dihydroxyphenyl and $R^{11}$, wherein $R^{11}$ is a member selected from the group consisting of —A—$NR^{13}R^{14}$, —$CONHR^{15}$, —A—S—$R^{16}$ and —$COOR^{17}$, wherein A denotes a lower alkylene group;

$R^{13}$ and $R^{14}$ are members independently selected from the group consisting of hydrogen, $(C_1-C_6)$alkyl, cycloalkyl and a sulfur- and a nitrogen-containing 5- or 6-membered heterocyclic ring, wherein said heterocyclic ring may be optionally substituted by one or two hydroxyl groups, or, alternatively, $R^{13}$ and $R^{14}$ together with the nitrogen to which they are bound form a pyrrolidine, piperidine or morpholine ring;

$R^{15}$ is a member selected from the group consisting of hydrogen and optionally substituted $(C_1-C_6)$alkyl;

$R^{16}$ is a member selected from the group consisting of $(C_1-C_6)$alkyl and a sulfur- and nitrogen containing 5- or 6-membered heterocyclic ring wherein said heterocyclic ring may be optionally substituted by one or two hydroxyl groups, carboxyl groups, or $(C_1-C_6)$ alkoxycarbonyl groups;

$R^{17}$ is optionally substituted $(C_1-C_6)$alkyl;

$R^{23}$ is a member selected from the group consisting of hydrogen and optionally substituted $(C_1-C_6)$alkyl;

$R^{24}$ is a member selected from the group consisting of phenyl, benzyl, and $R^{25}(CH_2)_sCH(T)(CH_2)_k$, or a heterocyclic ring having the formula

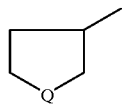

or alternatively, together with $R^{23}$ and the nitrogen atom to which they are bound form a 5- or 6-membered heterocyclic ring having the formula

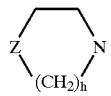

$R^{25}$ is either phenoxy or unsubstituted, monosubstituted, or disubstituted Ar, wherein, Ar is a member selected from the group consisting of phenyl, pyridinyl, furanyl, thiophenyl, naphthyl, each substituent of monosubstituted Ar is a member selected from the group consisting of hydroxy, $(C_1-C_6)$alkoxy, and $O(CH_2)_r CO_2R^{23}$, each substituent of disubstituted Ar is independently hydroxy or $(C_1-C_6)$alkoxy, Q is a member selected from the group consisting of $SO_2$, S, or O;

x is an integer from 1 to 5;

y is an integer from 1 to 5;

h is an integer from 1 to 2;

k is an integer from 1 to 7;

r is an integer from 1 to 2;

s is a integer from 0 to 6;

T is either hydrogen or OH;

Z is a member of the group consisting of $CH_2$, O, NH, $NCH_3$, and

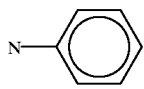

q is an integer from 0 to 1;

n is an integer from 0 to 5;

t is an integer from 0 to 1;

m is an integer from 0 to 2;

p is an integer from 0 to 1;

z is an integer from 0 to 1; provided that (1) at least one of x and y is one and (2) s plus k total no more than 7.

27. A method in accordance with claim 26, wherein

Y is S;

X is a member selected from the group consisting of O, S and $NR^6$, wherein $R^6$ a member selected from the group consisting hydrogen and optionally substituted $(C_1-C_6)$alkyl;

R is a member selected from the group consisting of hydrogen and 3,4-dihydroxyphenyl;

$R^1$ and $R^3$ are each hydroxy;

$R^2$ and $R^4$ are each hydrogen;

q is an integer from 0 to 1;

n is an integer from 0 to 5;

t is an integer from 0 to 1;

m is an integer from 0 to 2;

p is an integer from 0 to 1; and z is 0.

28. A method in accordance with claim 27, wherein

Y is S;

R is 3,4-dihydroxyphenyl;

q is 1;

n is 1 to 5;

t is 0;

m is 0; and p is 0.

29. A method in accordance with claim 27, wherein

Y is S;

R is 3,4-dihydroxyphenyl;

q is 0;

n is 1 to 5;

t is 0;

m is 0; and p is 0.

30. A method of treating a PPARγ mediated disease, said method comprising administering in combination therapy, a therapeutically effective amount of a compound of the formula

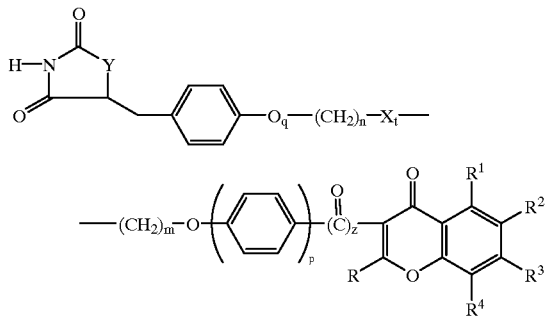

I wherein:

Y is S;

X is a member selected from the group consisting of O, S and $NR^6$, wherein $R^6$ is a member selected from the group consisting hydrogen and optionally substituted $(C_1-C_{10})$alkyl;

$R^1$, $R^2$, $R^3$ and $R^4$ are members independently selected from the group consisting of hydrogen, hydroxy, halogen, optionally substituted $(C_1-C_6)$alkyl, optionally substituted $(C_1-C_{20})$alkoxy, $(C_1-C_6)$ alkylcarbonyl, $(C_1-C_{20})$alkenyl, $R^{24}R^{23}N(CH_2)_xCH(OH)(CH_2)_yO$—, optionally substituted aroyl and aryl $(C_1-C_{10})$alkylcarbonyl;

R is a member selected from the group consisting of hydrogen, phenyl, 3,4-dihydroxyphenyl and $R^{11}$, wherein $R^{11}$ is a member selected from the group consisting of —A—$NR^{13}R^{14}$, —$CONHR^{15}$, —A—S—$R^{16}$ and —$COOR^{17}$, wherein A denotes a lower alkylene group;

$R^{13}$ and $R^{14}$ are members independently selected from the group consisting of hydrogen, $(C_1-C_6)$alkyl, cycloalkyl and a sulfur- and a nitrogen-containing 5- or 6-membered heterocyclic ring, wherein said heterocyclic ring may be optionally substituted by one or two hydroxyl groups, or, alternatively, $R^{13}$ and $R^{14}$ together with the nitrogen to which they are bound form a pyrrolidine, piperidine or morpholine ring;

$R^{15}$ is a member selected from the group consisting of hydrogen and optionally substituted ($C_1$–$C_6$)alkyl;

$R^{16}$ is a member selected from the group consisting of($C_1$–$C_6$)alkyl and a sulfur- and nitrogen containing 5- or 6-membered heterocyclic ring wherein said heterocyclic ring may be optionally substituted by one or two hydroxyl groups, carboxyl groups, or ($C_1$–$C_6$) alkoxycarbonyl groups;

$R^{17}$ is optionally substituted ($C_1$–$C_6$)alkyl;

$R^{23}$ is a member selected from the group consisting of hydrogen and optionally substituted ($C_1$–$C_6$)alkyl;

$R^{24}$ is a member selected from the group consisting of phenyl, benzyl, and $R^{25}(CH_2)_s CH(T)(CH_2)_k$, or a heterocyclic ring having the formula

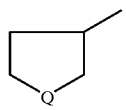

or alternatively, together with $R^{23}$ and the nitrogen atom to which they are bound form a 5- or 6-membered heterocyclic ring having the formula

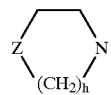

$R^{25}$ is either phenoxy or unsubstituted, monosubstituted, or disubstituted Ar, wherein, Ar is a member selected from the group consisting of phenyl, pyridinyl, furanyl, thiophenyl, naphthyl, each substituent of monosubstituted Ar is a member selected from the group consisting of hydroxy, ($C_1$–$C_6$)alkoxy, and $O(CH_2)_r CO_2R^{23}$, each substituent of disubstituted Ar is independently hydroxy or ($C_1$–$C_6$)alkoxy, Q is a member selected from the group consisting of $SO_2$, S, or O;

x is an integer from 1 to 5;

y is an integer from 1 to 5;

h is an integer from 1 to 2;

k is an integer from 1 to 7;

r is an integer from 1 to 2;

s is a integer from 0 to 6;

T is either hydrogen or OH;

Z is a member of the group consisting of $CH_2$, O, NH, $NCH_3$, and

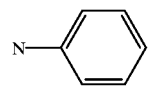

q is an integer from 0 to 1;

n is an integer from 0 to 5;

t is an integer from 0 to 1;

m is an integer from 0 to 2;

p is an integer from 0 to 1;

z is an integer from 0 to 1; provided that (1) at least one of x and y is one and (2) s plus k total no more than 7; and a member selected from the group consisting of a drug that bind to or modifies activity of a vitamin D receptor, a retinoid X receptor, or a retinoic acid receptor.

31. A method in accordance with claim 30, wherein said combination drug is a member selected from the group consisting of 9-cis-rctinoic acid, 13-cis-retinoic acid, all-trans-retinoic acid, tazarotene, Targretin, 1,25-dihydroxy-vitamin, calcipotriene, LG100268 and TTNPB.

* * * * *

UNITED STATES PATENT AND TRADEMARK OFFICE
CERTIFICATE OF CORRECTION

PATENT NO. : 6,028,088
DATED : February 22, 2000
INVENTOR(S) : Harrihar A. Pershadsingh and Mitchell A. Avery It is certified that error appears in the above-identified patent and that said Letters Patent is hereby corrected as shown below:

In claim 1, column 37, line 61, please delete "0" and insert therefor --1--.

In claim 13, column 39, line 10, please delete "0" and insert therefor the letter --O--.

In claim 22, column 40, line 11, please delete "—COOR$^7$" and insert therefor -—COOR$^{17}$--.

Signed and Sealed this

Eighth Day of May, 2001

Attest:

NICHOLAS P. GODICI

Attesting Officer

Acting Director of the United States Patent and Trademark Office